(12) United States Patent
Hayashida

(10) Patent No.: US 9,839,355 B2
(45) Date of Patent: Dec. 12, 2017

(54) METHOD OF PROCESSING INFORMATION, AND INFORMATION PROCESSING APPARATUS

(71) Applicant: FUJITSU LIMITED, Kawasaki-shi, Kanagawa (JP)

(72) Inventor: Naoko Hayashida, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 436 days.

(21) Appl. No.: 14/288,873

(22) Filed: May 28, 2014

(65) Prior Publication Data

US 2014/0359115 A1 Dec. 4, 2014

(30) Foreign Application Priority Data

Jun. 4, 2013 (JP) ................................ 2013-118337

(51) Int. Cl.
*G06F 15/173* (2006.01)
*A61B 5/00* (2006.01)
(Continued)

(52) U.S. Cl.
CPC .......... *A61B 5/0022* (2013.01); *A61B 5/0077* (2013.01); *A61B 5/11* (2013.01); *A61B 5/1116* (2013.01); *H04L 67/12* (2013.01)

(58) Field of Classification Search
CPC .............................. H04L 67/22; H04L 67/306
(Continued)

(56) References Cited

U.S. PATENT DOCUMENTS 7,054,849 B2 * 5/2006 Prokopenko ........... H04N 7/163
348/E7.061
7,945,619 B1 * 5/2011 Chawla .................. G06Q 10/10
348/14.08

(Continued)

FOREIGN PATENT DOCUMENTS

JP 2003-78899 3/2003
JP 2003-111106 4/2003
(Continued)

OTHER PUBLICATIONS

Stylianos Asteriadis et al., "Estimation of behavioral user state based on eye gaze and head pose—application in an e-learning environment", *Multimed Tools Appl* (2009), Published online: Oct. 25, 2008, pp. 469-493, vol. 41, Issue 3, Springer Science + Business Media, LLC.
(Continued)

*Primary Examiner* — Khanh Dinh
*Assistant Examiner* — Clarence McCray
(74) *Attorney, Agent, or Firm* — Staas & Halsey LLP

(57) ABSTRACT

A method of processing information includes: identifying a time span in a period of viewing a content based on detection results of the behavioral viewing states of the user viewing the content, the time span being a period, during which a behavioral viewing state of the user is not determined to be a positive state or a negative state; extracting a time period during which an index indicating one of the positive state and the negative state of the user has an unordinary value with respect to values of the other time periods in the time span; and estimating a time period, during which the user has quite possible been in at least one of the positive state and the negative state, based on the time period extracted by the extracting.

9 Claims, 23 Drawing Sheets

(51) Int. Cl.
*H04L 29/08* (2006.01)
*A61B 5/11* (2006.01)

(58) Field of Classification Search
USPC .......................................................... 709/224
See application file for complete search history.

(56) References Cited

U.S. PATENT DOCUMENTS

| | | | | |
|---|---|---|---|---|
| 8,460,090 | B1* | 6/2013 | Gilliland | G07F 17/3262 |
| | | | | 463/16 |
| 8,744,898 | B1* | 6/2014 | Hewett | G06Q 30/02 |
| | | | | 705/7.29 |
| 2003/0046255 | A1 | 3/2003 | Prokopenko et al. | |
| 2003/0154180 | A1* | 8/2003 | Case | G06Q 30/02 |
| 2006/0026207 | A1 | 2/2006 | Sakai et al. | |
| 2011/0081634 | A1* | 4/2011 | Kurata | G01C 21/20 |
| | | | | 434/236 |
| 2011/0137835 | A1* | 6/2011 | Ito | G06K 9/00335 |
| | | | | 706/12 |
| 2012/0143693 | A1* | 6/2012 | Chung | G06Q 30/0269 |
| | | | | 705/14.66 |
| 2012/0150888 | A1* | 6/2012 | Hyatt | G06F 17/30528 |
| | | | | 707/758 |
| 2012/0317066 | A1* | 12/2012 | Miyazaki | G06Q 50/10 |
| | | | | 706/46 |
| 2013/0018954 | A1* | 1/2013 | Cheng | G06Q 10/00 |
| | | | | 709/204 |
| 2013/0143185 | A1* | 6/2013 | Liu | G09B 19/00 |
| | | | | 434/236 |
| 2013/0167219 | A1* | 6/2013 | Jung | H04L 63/1458 |
| | | | | 726/13 |
| 2013/0219417 | A1* | 8/2013 | Gilson | H04N 21/258 |
| | | | | 725/12 |
| 2013/0325948 | A1* | 12/2013 | Chen | G06Q 50/01 |
| | | | | 709/204 |
| 2014/0105488 | A1* | 4/2014 | Geng | G06K 9/6265 |
| | | | | 382/161 |
| 2014/0341473 | A1* | 11/2014 | Lee | G06K 9/00268 |
| | | | | 382/195 |
| 2015/0142888 | A1* | 5/2015 | Browning | H04L 12/1831 |
| | | | | 709/204 |
| 2016/0005320 | A1* | 1/2016 | deCharms | G09B 19/00 |
| | | | | 434/236 |

FOREIGN PATENT DOCUMENTS

| | | |
|---|---|---|
| JP | 2006-41887 | 2/2006 |
| JP | 2006-293979 | 10/2006 |
| JP | 2010-94493 | 4/2010 |
| JP | 2011-193371 A | 9/2011 |
| JP | 2011-203975 A | 10/2011 |
| WO | 2009/021198 A1 | 2/2009 |

OTHER PUBLICATIONS

Japanese Office Action dated Feb. 28, 2017 in corresponding Japanese Patent Application No. 2013-118337 (4 pages) (3 pages English Translation).

* cited by examiner

USER MONITORING CAMERA DATA SEQUENCE

| RECORDING START TIME | RECORDING END TIME | USER | SCREEN | RECORDED IMAGE |
|---|---|---|---|---|
| 2012/7/12 11:00:02.40 | 2012/7/12 13:00:02.40 | userA | scrB | /tmp/movie.userA_201201211000240 |
| 2012/7/12 13:00:03.69 | 2012/7/12 14:30:01.47 | userA | scrB | /tmp/movie.userA_20120130003069 |
| ⋮ | ⋮ | ⋮ | ⋮ | ⋮ |

EYE GAZE TRACKING (VISUAL ATTENTION AREA) DATA SEQUENCE

| TIME | USER | SCREEN | VISUAL ATTENTION AREA ESTIMATION MAP |
|---|---|---|---|
| 2012/7/12 11:00:01.30 | userA | scrB | /tmp/map.userA_2012071211000130 |
| 2012/7/12 11:00:01.69 | userA | scrB | /tmp/map.userA_2012071211000169 |
| ⋮ | ⋮ | ⋮ | ⋮ |

USER-SCREEN DISTANCE DATA SEQUENCE

| TIME | USER | SCREEN | DISTANCE DATA |
|---|---|---|---|
| 2012/7/12 11:00:03.70 | userA | scrB | 150 |
| 2012/7/12 11:00:03.72 | userA | scrB | 200 |
| ⋮ | ⋮ | ⋮ | ⋮ |

SCREEN COORDINATES

| TIME | USER | SCREEN | WINDOW ID | UPPER LEFT x COORDINATE | UPPER LEFT y COORDINATE | WIDTH | HEIGHT | OVERLAYING ORDER |
|---|---|---|---|---|---|---|---|---|
| 2012/7/12 11:00:01.30 | userA | scrB | 1 | 10 | 10 | 300 | 300 | 1 |
| 2012/7/12 11:00:01.30 | userA | scrB | 2 | 100 | 10 | 500 | 500 | 2 |
| 2012/7/12 11:00:01.69 | userA | scrB | 1 | 10 | 10 | 300 | 1000 | 1 |
| ⋮ | ⋮ | ⋮ | ⋮ | ⋮ | ⋮ | ⋮ | ⋮ | ⋮ |

DISPLAYED CONTENT LOG

| TIME | USER | SCREEN | WINDOW ID | CONTENT ID | CONTENT TIMEFRAME |
|---|---|---|---|---|---|
| 2012/7/12 11:00:01.30 | userA | scrB | 1 | 1 | 1 |
| 2012/7/12 11:00:01.30 | userA | scrB | 2 | 2 | 100 |
| 2012/7/12 11:00:01.69 | userA | scrB | 1 | 1 | 2 |
| ⋮ | ⋮ | ⋮ | ⋮ | ⋮ | ⋮ |

CONTENT

| CONTENT ID | URI |
|---|---|
| 1 | file://localhost/drive/c/movie1.avi |
| 2 | file://localhost/drive/c/meetingmat.pdfi |
| ⋮ | ⋮ |

MOVEMENT OF FACE PARTS

| TIME (START) | TIME (END) | USER | SCREEN | BLINKING | EYEBROW | ... |
|---|---|---|---|---|---|---|
| 2012/7/12 11:00:01.30 | 2012/7/12 11:00:01.69 | userA | scrB | MID | MID | ... |
| ⋮ | ⋮ | ⋮ | ⋮ | ⋮ | ⋮ | ⋮ |

EYE GAZE

| TIME (START) | TIME (END) | USER | SCREEN | WINDOW ID | FIXATION TIME (msec) | TOTAL AREA OF VIEWED CONTENT |
|---|---|---|---|---|---|---|
| 2012/7/12 11:00:01.30 | 2012/7/12 11:00:01.69 | userA | scrB | 1 | 10 | 8000 |
| ⋮ | ⋮ | ⋮ | ⋮ | ⋮ | ⋮ | ⋮ |

POSTURE CHANGE

| TIME (START) | TIME (END) | USER | SCREEN | WINDOW ID | USER-SCREEN DISTANCE (mm) | POSTURE CHANGE FLAG | POSTURE CHANGE TIME (msec) |
|---|---|---|---|---|---|---|---|
| 2012/7/12 11:00:01.30 | 2012/7/12 11:00:01.69 | userA | scrB | 1 | +20 | FALSE | 0 |
| 2012/7/12 11:00:01.69 | 2012/7/12 11:00:01.99 | userA | scrB | 1 | +100 | TRUE | 300 |
| 2012/7/12 11:00:01.99 | 2012/7/12 11:00:02.29 | userA | scrB | 1 | +105 | TRUE | 600 |
| 2012/7/12 11:00:02.29 | 2012/7/12 11:00:02.59 | userA | scrB | 1 | -5 | FALSE | 0 |
| ⋮ | ⋮ | ⋮ | ⋮ | ⋮ | ⋮ | ⋮ | ⋮ |

| CONTENT TIMEFRAME | 1 | 2 | 3 | 4 | 5 | 6 | ... | m | m+1 |
|---|---|---|---|---|---|---|---|---|---|
| USER STATUS | - | P | P | - | P | - | ... | N | - |

| CONTENT TIMEFRAME | 5 | 6 | 7 | 8 | 9 | ... | m |
|---|---|---|---|---|---|---|---|
| PNN TRANSITION VALUE (LOCAL MAXIMAL VALUE OF POSTURE CHANGE TIME IN TIMEFRAME) | / | 2200 | 2400 | 2450 | 800 | ... | 3800 |
| UNORDINARY PNN TRANSITION SECTION DETERMINATION RESULT | / | | | | UNORDINARY PNN TRANSITION SECTION | ... | | t0=2012/7/12 11:00:01.30 t1=2012/7/12 11:00:01.69

/tmp/map.userA_2012071211100000169

GROUP1

GROUP2

GROUP3

FIG. 18

| CONTENT TIMEFRAME | $t_{m1}$ | $t_{m1+1}$ | $t_{m1+2}$ | ... | $t_{m1+n}$ |
|---|---|---|---|---|---|
| GROUP1 | [0.1] | [0.4] | [0.3] | ... | [0.1] |
| GROUP2 | [0.2] | UNORDINARY SECTION [0.5] | UNORDINARY SECTION [0.8] | ... | UNORDINARY SECTION [0.6] |
| GROUP3 | UNORDINARY SECTION [0.5] | [0.2] | UNORDINARY SECTION [0.5] | ... | UNORDINARY SECTION [0.7] |

FIG. 21

| HIGH NEUTRAL PLUS ESTIMATION VALUE TIMEFRAME | $t_{h1}$ | $t_{h1+1}$ | ... | $t_{h1+j}$ |
|---|---|---|---|---|
| SELECTED DATA | 150 | 120 | ... | 100 |
| ORIGINAL DATA | 140 | 10 | ... | 120 |
| ATTRIBUTE THAT IS REMARKABLY POSITIVE THAN NEUTRAL | | ATTRIBUTE C | ... | |

FIG. 23

| CONTENT TIMEFRAME | $t_{m1+1}$ | ... | $t_{m1+k}$ | $t_{m1+k+1}$ | $t_{m1+k+2}$ | $t_{m1+k+3}$ | ... |
|---|---|---|---|---|---|---|---|
| ONE TIME CONSTANT PERIOD UPPER: PNN TRANSITION VALUE LOWER: DEGREE OF UNORDINARY TIMEFRAME | 2200 | ... | 2300 | 2200 | 2000 | 2400 | ... |
| | 0 | ... | 125 | 150 | 175 | 250 | ... |
| | : | : | : | : | : | : | : |
| FOUR TIMES INTERVAL LENGTH UPPER: PNN TRANSITION VALUE LOWER: DEGREE OF UNORDINARY TIMEFRAME | | | 2537 | | | | |
| | | | 438 | | | | |
| | : | : | : | : | : | : | : |
| UNORDINARY SECTION DETERMINATION (TIME CONSTANT PERIOD TO BE GROUNDS) | | | UNORDINARY SECTION (FOUR TIMES CONSTANT PERIOD) | | | | |

METHOD OF PROCESSING INFORMATION, AND INFORMATION PROCESSING APPARATUS

CROSS-REFERENCE TO RELATED APPLICATION

This application is based upon and claims the benefit of priority of the prior Japanese Patent Application No. 2013-118337, filed on Jun. 4, 2013, the entire contents of which are incorporated herein by reference.

FIELD

The embodiments discussed herein are related to a method of processing information, and an information processing apparatus.

BACKGROUND

To date, proposals have been made on techniques for determining a degree of attention of a user to a content using a biosensor and a captured image. In the case of using a biosensor, methods of determining a degree of concentration of a user based on GSR (Galvanic Skin Response), Skin temperature, and BVP (Blood Volume Pulse) have been known. In the case of using an image, methods of calculating a degree of enthusiasm of a user by a posture of the user (leaning forward and leaning back) have been known.

As examples of related-art techniques, Japanese Laid-open Patent Publication Nos. 2003-111106 and 2006-41887 have been known.

SUMMARY

According to an aspect of the invention, a method of processing information includes: identifying a time span in a period of viewing a content based on detection results of the behavioral viewing states of the user viewing the content, the time span being a period, during which a behavioral viewing state of the user is not determined to be a positive state or a negative state; extracting a time period during which an index indicating one of the positive state and the negative state of the user has an unordinary value with respect to values of the other time periods in the time span; and estimating a time period, during which the user has quite possible been in at least one of the positive state and the negative state, based on the time period extracted by the extracting.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 illustrates an example of a data structure of an attentive audience sensing data DB;

FIG. 5 illustrates an example of a data structure of a displayed contents log DB;

FIG. 6 illustrates an example of a data structure of a user's audio/visual action state variable DB;

FIG. 7 illustrates an example of a data structure of a user status determination result DB;

FIG. 8 illustrates an example of a data structure of an unordinary PNN transition section DB;

FIG. 18 is a table illustrating determination results of unordinary PNN transition section for each individual groups, which are totaled in audio/visual digital content timeframes $t_{m1}$ to $t_{m1+n}$;

FIG. 21 is a table that is generated by the processing illustrated in FIG. 20;

FIG. 23 is a table illustrating an example of comparison of PNN transition values and determination results of an unordinary PNN transition section in multiple constant period according to the fifth embodiment.

DESCRIPTION OF EMBODIMENTS

In the case of using a captured image in order to determine a degree of attention of a user to a content, when it is expected that the user will be get excited very much as a characteristic of the content to be displayed, it is possible to determine the state of the user using a simple model. For example, if the user has an interest or attention, the user tends to lean forward, whereas if the user has no interest or attention, the user tends to lean back.

However, when a content to be viewed is not a content that is not expected to gets the user excited very much, such as e-learning or a lecture video, it is difficult to determine whether the user has an interest or attention from his or her appearance/behavior. Accordingly, it is also difficult to definitely determine whether the user is interested or not from the captured images of the state of a user.

According to an embodiment of the present disclosure, it is desirable to provide a method of processing information, and an information processing apparatus that allow a precise estimation of the state of a user who is viewing a content.

First Embodiment

In the following, a detailed description will be given of a first embodiment of an information processing system with reference to FIG. 1 to FIG. 15. An information processing system 100 according to the first embodiment is a system in which estimation is made of a state of a user who has viewed a content in order to utilize the estimation result. For example, an estimation is made of a time period in which the user was in a state (positive) of having an interest or attention in the content, a time period in which the user in a state (negative) of not having an interest or attention in the content, or a time period in which the user had a high possibility of having been interested or paying attention to the content, and so on.

Figure 1:
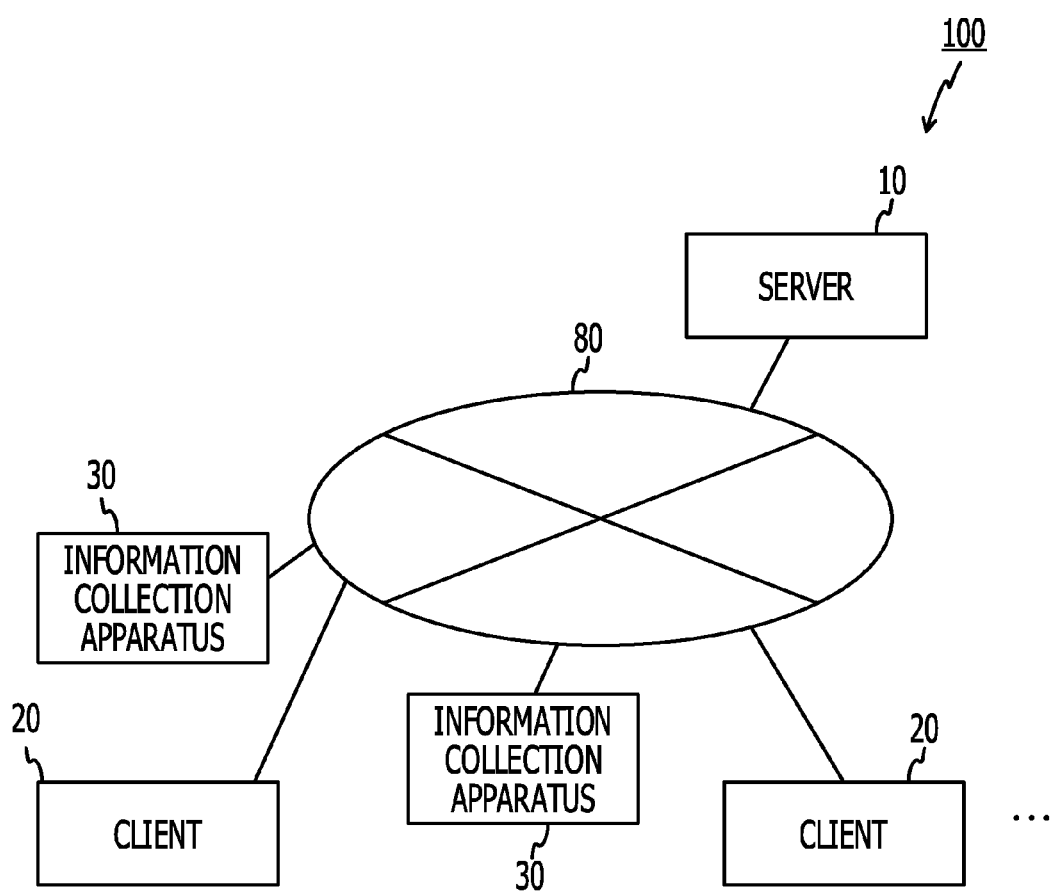
FIG. 1 schematically illustrates a configuration of an information processing system according to a first embodiment.

FIG. 1 illustrates a schematic configuration of the information processing system 100. As illustrated in FIG. 1, the information processing system 100 includes a server 10 as an information processing apparatus, clients 20, and information collection apparatuses 30. The server 10, the clients 20, and the information collection apparatuses 30 are connected to a network 80, such as the Internet, a local area network (LAN), and so on.

Figure 2A:
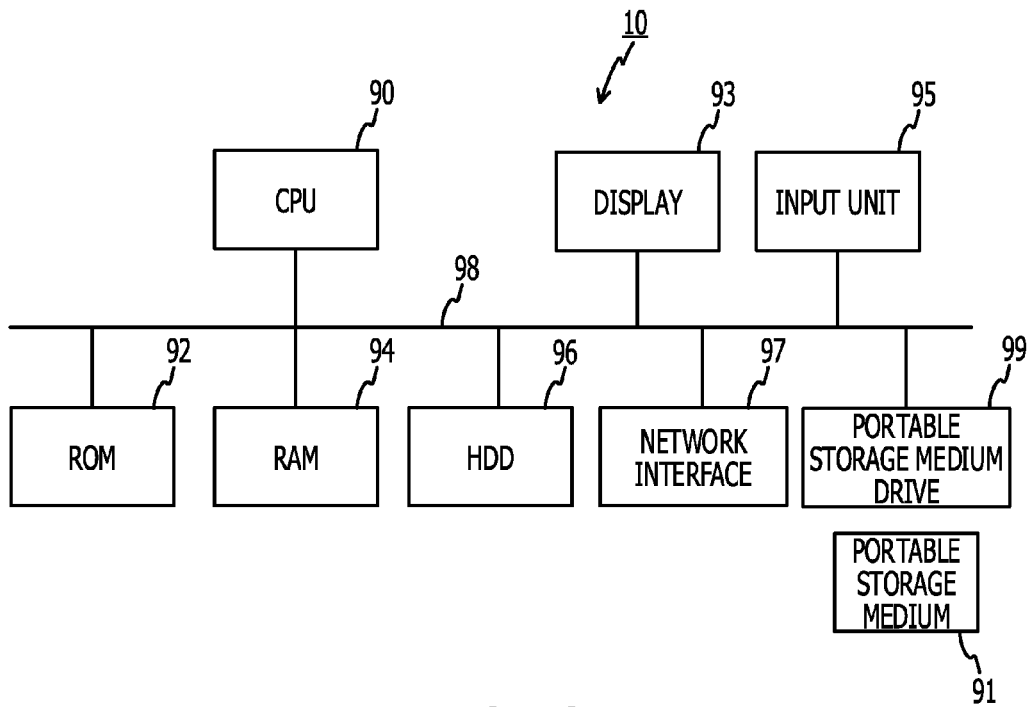
FIG. 2A illustrates a hardware configuration of a server.
Figure 3:
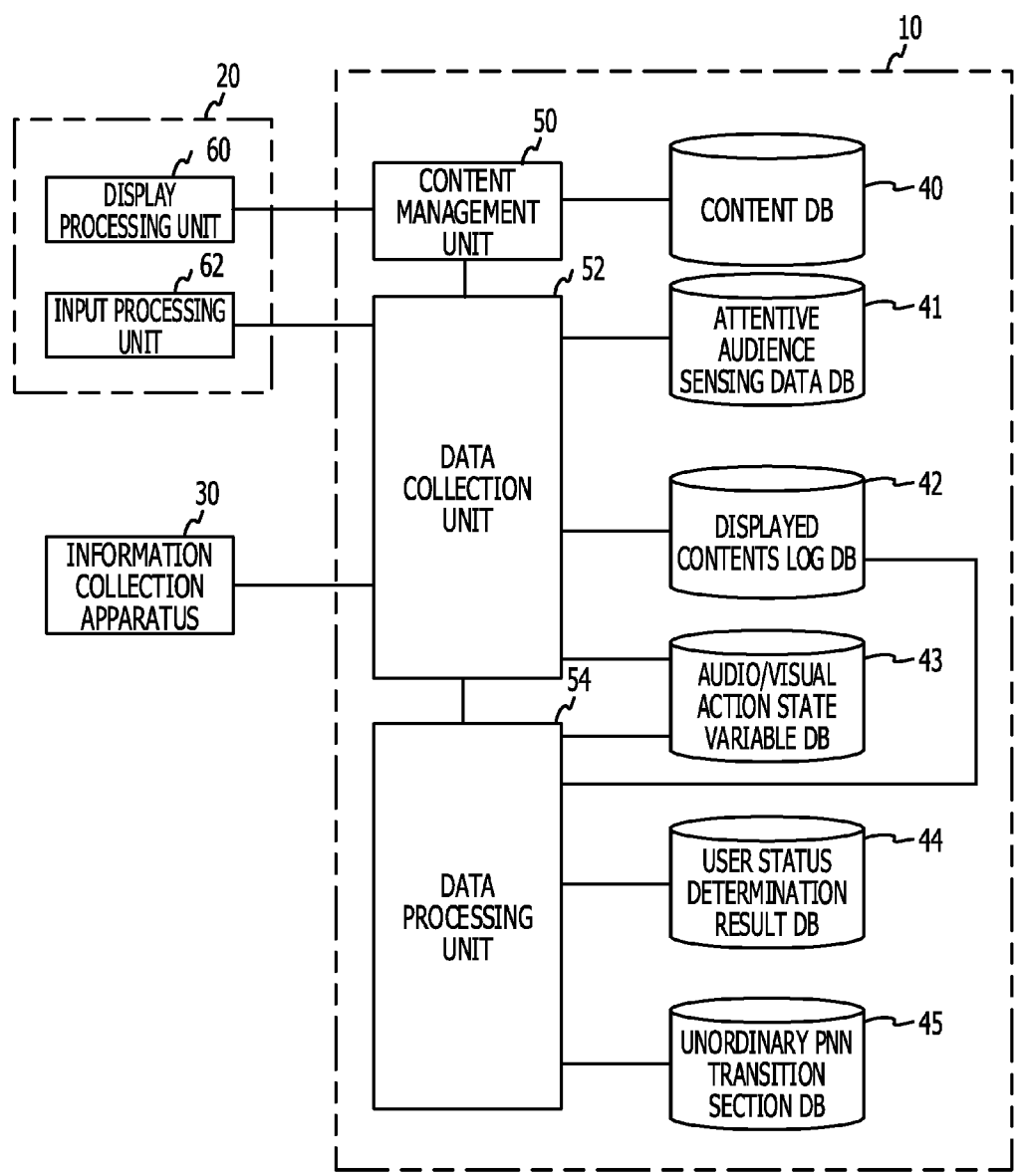
FIG. 3 is a functional block diagram of the information processing system.

The server 10 is an information processing apparatus on which server software is deployed (installed), and which aggregates, provides index and stores, and classifies data on the user states, and performs various calculations on the data. Also, the server 10 manages content distribution including control of the display mode of the content to be distributed to the users. FIG. 2A illustrates a hardware configuration of the server 10. As illustrated in FIG. 2A, the server 10 includes a central processing unit (CPU) 90, a read only memory (ROM) 92, a random access memory (RAM) 94, a storage unit (here, a hard disk drive (HDD)) 96, a display 93, an input unit 95, a network interface 97, a portable storage medium drive 99, and so on. Each of these components of the server 10 is connected to a bus 98. The display 93 includes a liquid crystal display, or the like, and the input unit 95 includes a keyboard, a mouse, a touch panel, and so on. In the server 10, the CPU 90 executes programs (including an information processing program) that are stored in the ROM 92 or the HDD 96, or programs (including an information processing program) that are read by the portable storage medium drive 99 from the portable storage medium 91 so as to achieve functions as a content management unit 50, a data collection unit 52, and a data processing unit 54, which are illustrated in FIG. 3. In this regard, FIG. 3 illustrates a content database (DB) 40, an attentive audience sensing data database (DB) 41, a displayed contents log database (DB) 42, a user's audio/visual action state variable database (DB) 43, a user status determination result database (DB) 44, and an unordinary PNN transition section database (DB) 45, which are stored in the HDD 96 of the server 10, and so on. In this regard, descriptions will be given later of specific data structures, and so on of the individual DBs 40, 41, 42, 43, 44, and 45.

The content management unit 50 provides a content (for example, a lecture video) stored in the content DB 40 to the client 20 (a display processing unit 60) in response to a demand from a user of the client 20. The content DB 40 stores data of various contents.

The data collection unit 52 collects information on a content that the user has viewed from the content management unit 50, and collects data on a state of the user while the user is viewing the content from the information collection apparatus 30. Also, the data collection unit 52 stores the collected information and data into the attentive audience sensing data DB 41, the displayed contents log DB 42, and the user's audio/visual action state variable DB 43. In this regard, the data collection unit 52 collects attentive audience sensing data, such as a user monitoring camera data sequence, an eye gaze tracking (visual attention area) data sequence, a user-screen distance data sequence and, so on as data on the state of the user.

The data processing unit 54 determines a timeframe in which the user who has been viewing the content was in a positive state and a timeframe in which the user was in a negative state based on the data stored in the displayed contents log DB 42 and the data stored in the user's audio/visual action state variable DB 43. Also, the data processing unit 54 estimates a timeframe (unordinary PNN transition section) having a high possibility of the user having been in a positive state. The data processing unit 54 stores a determination result and an estimation result in the user status determination result DB 44 and the unordinary PNN transition section DB 45, respectively.

Figure 2B:
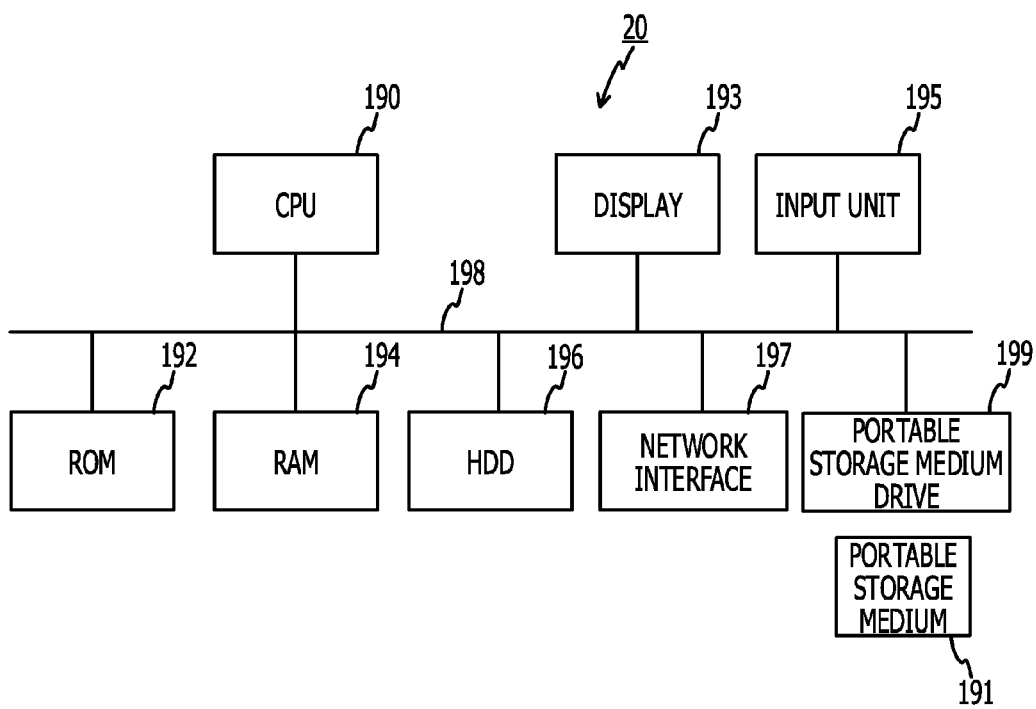
FIG. 2B illustrates a hardware configuration of a client.

The client 20 is an information processing apparatus in which client software is disposed (installed), and is an apparatus which displays and manages a content for the user, and stores viewing history. As the client 20, it is possible to employ a mobile apparatus, such as a mobile phone, a smart phone, and the like in addition to a personal computer (PC). FIG. 2B illustrates a hardware configuration of the client 20. As illustrated in FIG. 2B, the client 20 includes a CPU 190, a ROM 192, a RAM 194, a storage unit (HDD) 196, a display 193, an input unit 195, a network interface 197, a portable storage medium drive 199, and the like. Each component in the client 20 is connected to a bus 198. In the client 20, the CPU 190 executes the programs stored in the ROM 192 or the HDD 196, or the programs that are read by the portable storage medium drive 199 from the portable storage medium 191 so that the functions as the display processing unit 60 and the input processing unit 62, which are illustrated in FIG. 3, are achieved.

The information collection apparatus 30 is an apparatus for collecting data on a state of the user, and includes a Web camera, for example. The information collection apparatus 30 transmits data on the collected user states to the server 10 through the network 80. In this regard, the information collection apparatus 30 may be incorporated in a part of the client 20 (for example, in the vicinity of the display).

In this regard, in the present embodiment, in the client 20, information display in accordance with a user is performed on the display 193. Also, information collection from a user of the client 20 is stored in the information processing system 100 in association with the user. That is to say, the client 20 is subjected to access control by client software or server software. Accordingly, in the present embodiment, information collection and information display are performed on the assumption of the confirmation that the user of the client 20 is "user A", for example. Also, in the client 20, information display is performed in accordance with the display 193. Also, information collected from the client 20 is stored in the information processing system 100 in association with the display 193. That is to say, information collection and information display are performed on the assumption that the client 20 is recognized by the client software or the server software, and the display 193 is confirmed to be a predetermined display (for example, screen B (scrB)).

Next, descriptions will be given of the data structures of the DBs 41, 42, 43, 44, and 45 accessed by the server 10 with reference to FIGS. 4, 5, 6, 7, and 8.

FIG. 4 illustrates an example of a data structure of the attentive audience sensing data DB 41. The attentive audience sensing data DB 41 stores attentive audience sensing data that has been collected by the data collection unit 52 through the information collection apparatus 30. As illustrated in FIG. 4, the attentive audience sensing data DB 41 stores "user monitoring camera data sequence", "eye gaze tracking (visual attention area) data sequence", and "user-screen distance data sequence" as an example.

The user monitoring camera data sequence is a recorded state of the user while the user was viewing a content as data. Specifically, the user monitoring camera data sequence includes individual fields such as "recording start time", "recording end time", "user", "screen", and "recorded image", and stores the state of the user (A) who is viewing the content displayed on the display (for example, screen B) in a moving image format. In this regard, in the user monitoring camera data sequence, an image sequence may be stored.

The eye gaze tracking (visual attention area) data sequence stores a "visual attention area estimation map", which is obtained by observing an eye gaze of the user at each time, for example. In this regard, although it is possible to achieve observation of the eye gaze using a special device that measures an eye movement. However, it is possible to detect user's gaze location using a marketed Web camera (assumed to be disposed at the upper part of the display (screen B) of the client 20) included in the information collection apparatus 30 (for example, refer to Stylianos Asteriadis et al., "Estimation of behavioral user state based on eye gaze and head pose-application in an e-learning environment", Multimed Tools Appl, 2009). In these gaze detection techniques, visually focused data focused on a content is represented as data called a heat map in which a time period during which visual focused points is represented by an area of a circle and intensity of overlay (refer to FIG. 12D). In the present embodiment, a circle that contains all the plurality of positions on which visual focused points is recorded as visually focused point information for each of the unit time with a center of gravity of a plurality of positions on which visual focused points per unit time as a center. Here, in a visual attention area estimation map recorded at time $t_1$, circle information that has been recorded since time $t_0$ is recorded in the file thereof. In the case where five pieces of visually focused point information is recorded from time $t_0$ to time $t_1$, up to five pieces of circle information is recorded (refer to FIG. 12D).

The user-screen distance data sequence records, for example, a distance measurement result between a user (A) who is viewing a content and a screen (screen B) on which the content is displayed. The distance measurement may be performed using a distance sensing special device, such as a laser beam or a depth sensing camera. However, a user monitoring camera data sequence captured by a Web camera included in the information collection apparatus 30 may be used as a measurement. If a user monitoring camera data sequence captured by a Web camera is used, it is possible to use an accumulated value of a change of the size of a rectangular area enclosing a face of the user multiplied by a coefficient as a distance.

FIG. 5 illustrates an example of a data structure of the displayed contents log DB 42. The user sometimes views a plurality of screens at the same time, or sometimes displays a plurality of windows on one screen. Accordingly, the displayed contents log DB 42 stores in what state windows are disposed on a screen, and which content is displayed in a window as a history. Specifically, as illustrated in FIG. 5, the displayed contents log DB 42 includes tables of "screen coordinates", "displayed content log", and "content".

The "screen coordinates" table records "overlaying order" of windows in addition to "window IDs" of the windows displayed on a screen, "upper-left x coordinate" and "upper-left y coordinate" indicating a display position, "width" and "height" indicating a size of a window. In this regard, the reason why "overlaying order" is recorded is that even if a content is displayed in a window, there are cases where a window is hidden under another window, and thus a window that is not viewed by the user sometimes exists on a screen.

The "displayed content log" table records "window IDs" of the windows that are displayed on a screen, and "content ID" and "content timeframe" of a content that is displayed on the windows. The "content timeframe" records which section (timeframe) of a content is displayed. In this regard, for "content ID", the content ID defined in "content" table in FIG. 5 is stored.

FIG. 6 illustrates an example of a data structure of the user's audio/visual action state variable DB 43. The user's audio/visual state variable is used as a variable of the user state. In FIG. 6, the user's audio/visual action state variable DB 43 has tables of "movement of face parts", "eye gaze", and "posture change" as an example.

The "movement of face parts" table includes fields, such as "time (start)", "time (end)", "user", "screen", "blinking", "eyebrow", . . . , and so on. The "movement of face parts" table stores information, such as whether blinking and eyebrow movement was active, moderate, and so on during the time from "time (start)" to "time (end)".

The "eye gaze" table includes fields of "time (start)", "time (end)", "user", "screen", "window ID", "fixation time (msec)", and "total area of viewed content". Here, the "fixation time (msec)" means a time period during which a user fixates his/her eye gaze. Also, "total area of viewed content" means a numeric value representing the amount of each content viewed by the user, and the details thereof will be described later.

The "posture change" table includes fields of "time (start)", "time (end)", "user", "screen", "window ID", "user-screen distance", "posture change flag", and "posture change time". The detailed descriptions will be given later of "user-screen distance", "posture change flag", and "posture change time", respectively.

FIG. 7 illustrates an example of a data structure of the user status determination result DB 44. The user status determination result DB 44 records in which status the user was for each content timeframe. For a user status, if in a positive state, "P" is recorded, if in a negative state, "N" is recorded, and if in a state which is neither positive nor negative (neutral state), "-" is recorded.

FIG. 8 illustrates an example of a data structure of the unordinary PNN transition section DB 45. The unordinary PNN transition section DB 45 records a timeframe (unordinary PNN transition section) that is allowed to be estimated as highly possible to be positive although in a state which is neither positive nor negative (neutral state) in the user status determination result DB 44. A description will be later given of specific contents of the unordinary PNN transition section DB 45.

Next, a description will be given of processing that is executed on the server 10.

Attentive Audience Sensing Data Collection/Management Processing

First, a description will be given of attentive audience sensing data collection/management processing executed by the data collection unit 52 with reference to a flowchart in FIG. 9.

Figure 9:
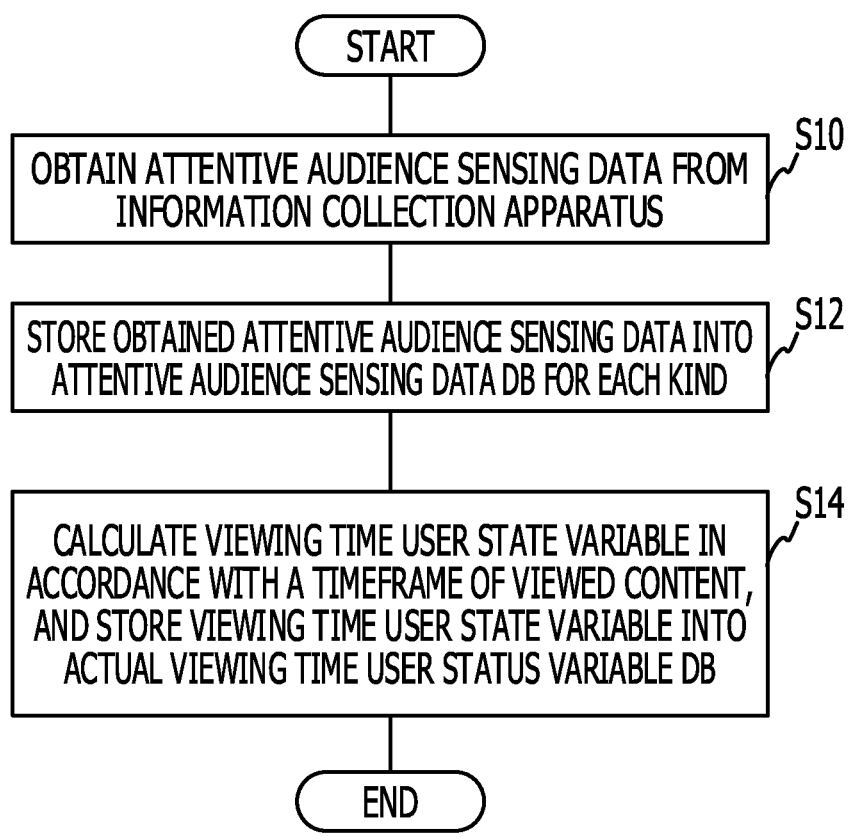
FIG. 9 is a flowchart of attentive audience sensing data collection and management processing executed by a data collection unit.

In the processing in FIG. 9, first, in step S10, the data collection unit 52 obtains attentive audience sensing data from the information collection apparatus 30. Next, in step S12, the data collection unit 52 stores the obtained attentive audience sensing data into the attentive audience sensing data DB 41 for each kind (for each user monitoring camera data sequence, eye gaze tracking (visual attention area) data sequence, and user-screen distance data sequence).

Next, in step S14, the data collection unit 52 calculates a user's audio/visual action state variable at viewing time in accordance with a timeframe of the audio/visual digital contents, and stores the user's audio/visual action state variable into the user's audio/visual action state variable DB 43.

Here, various kinds of processing is assumed in accordance with the kinds of data collected as step S14. In the present embodiment, descriptions will be given of processing for calculating the posture change flag and the posture change time in the "posture change" table in FIG. 6 (the posture change evaluation value calculation processing), and processing for calculating the total area of viewed content in the "eye gaze" table in FIG. 6 (total viewing area calculation processing).

Posture Change Evaluation Value Calculation Processing

A description will be given of posture change evaluation value calculation processing executed by the data collection unit 52 with reference to a flowchart with reference to FIG. 10.

Figure 10:
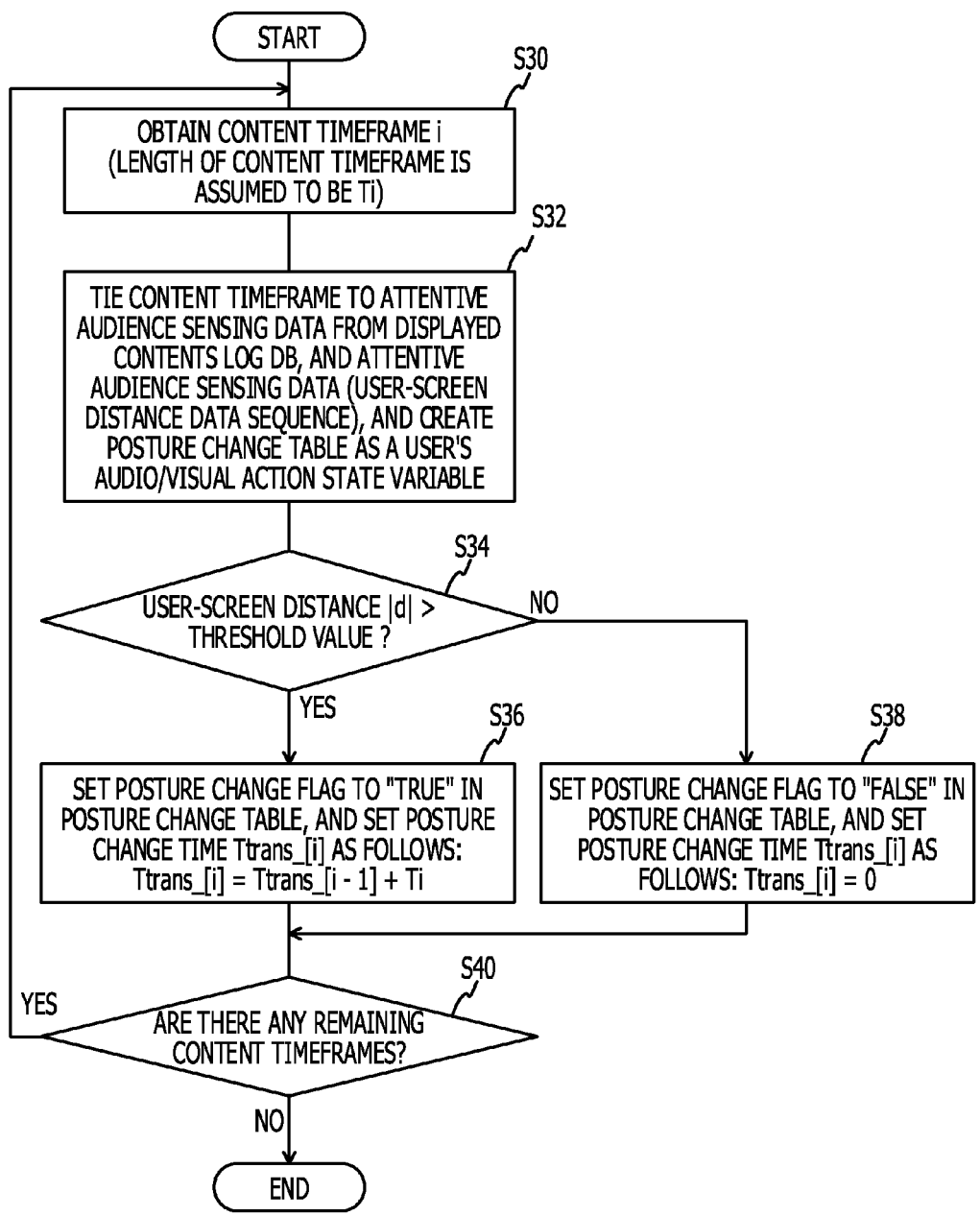
FIG. 10 is a flowchart of posture change evaluation value calculation processing executed by the data collection unit.

In the processing in FIG. 10, first, in step S30, the data collection unit 52 obtains a content timeframe i. In this regard, it is assumed that the length of the content timeframe i is Ti.

Next, in step S32, the data collection unit 52 ties a content timeframe and attentive audience sensing data from the displayed contents log DB 42, the user-screen distance data sequence in the attentive audience sensing data DB 41, and creates a posture change table as a user's audio/visual action state variable. In this case, data is input into each field of "time (start)", "time (end)", "user", "screen", "window ID", and "user-screen distance" of the posture change table in FIG. 6. In this regard, data of the amount of change from a reference position (a position where the user is ordinary positioned) is input in the field of "user-screen distance".

Next, in step S34, the data collection unit 52 determines whether a user-screen distance |d| is greater than a threshold value. Here, it is possible to employ a reference position× (1/3)=50 mm, and so on for the threshold value, for example.

In step S34, if it is determined that the user-screen distance is larger than the threshold value, the processing proceeds to step S36, and the data collection unit 52 sets the posture change flag to "true" in the posture change table. Also, the data collection unit 52 sets posture change time $T_{trans\_[i]}$ of the content timeframe i as follows: $T_{trans\_[i]} = T_{trans\_[i]} + Ti$. In this regard, in the posture change table in FIG. 6, the posture change flag of the second data, and the third data from top becomes "true", and 600 (msec) in the timeframe 2012/7/12 11:00:01.69 to 2012/7/12 11:00:02.29 is recorded as posture change time.

On the other hand, in step S34, if it is determined that the user-screen distance is less than the threshold value, the processing proceeds to step S38, and the data collection unit 52 sets the posture change flag to "false" in the posture change table. Also, the data collection unit 52 sets the posture change time $T_{trans\_[i]}$ as follows: $T_{trans\_[i]} = 0$ (for example, refer to the fourth data from the top in the posture change table in FIG. 6).

Next, in step S40, the data collection unit 52 determines whether there remains a content timeframe whose posture change evaluation value is to be calculated. Here, if it is determined that there remains a content time frame whose posture change evaluation value is to be calculated, the processing returns to step S30, and the above-described processing is repeated, otherwise all the processing in FIG. 10 is terminated.

Total Viewed Area Calculation Processing

Next, a description will be given of processing for calculating "total area of viewed content" in the eye gaze table in FIG. 6, which is executed by the data collection unit 52, (total viewed area calculation processing) with reference to a flowchart in FIG. 11. Here, a description will be given of the case of calculating the total viewed area of the content having a content ID=Z (=1) displayed in the window having the window ID=Y (=1) on the screen X (=scrB) at time t1.

Figure 12A:
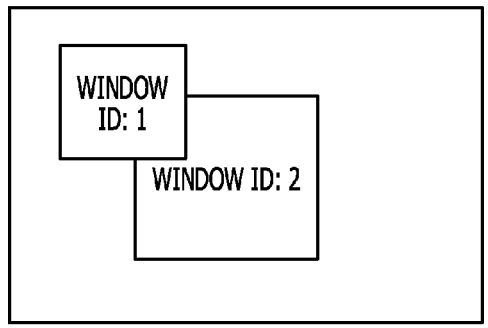
FIGS. 12A, 12B, 12C, 12D and 12E are explanatory diagrams of the processing illustrated in FIG. 11.
Figure 12B:
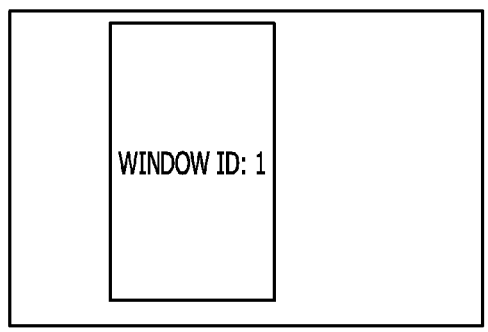
Figure 12C:
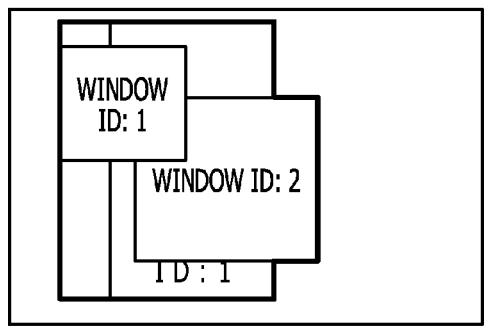
Figure 12D:
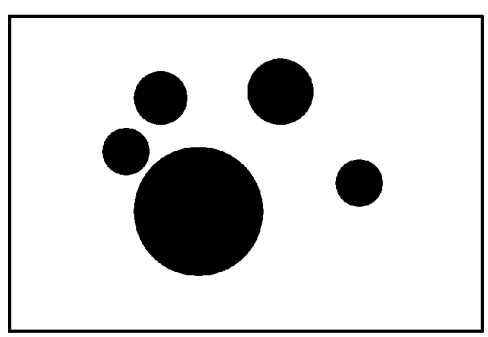

In this regard, it is assumed that, as illustrated in FIG. 12A, there are two windows on the screen B at time $t_0$, and as illustrated in FIG. 12B, there is one window on the screen B at time t1. Here, there is no record as to at what timing from time $t_0$ to $t_1$, the window having the window ID: 2 has disappeared. Accordingly, it is not possible to correctly calculate the amount of time during which the contents having the content ID=1 and content ID=2, which are displayed in the window ID: 1 and the window ID: 2, respectively, were viewed. Accordingly, in the present embodiment, on the assumption that a time period from time $t_0$ to $t_1$ is very small, the total viewed area at the point in time $t_1$, is calculated only on a content that is displayed in the window existing at time $t_1$.

Figure 11:
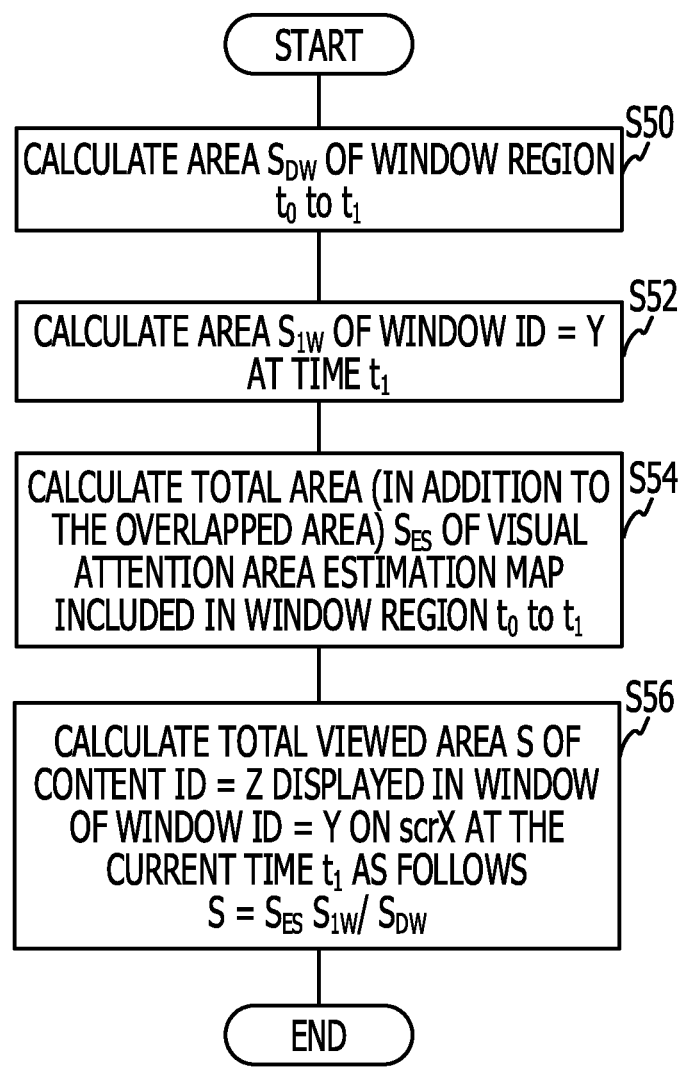
FIG. 11 is a flowchart of total viewing area calculation processing executed by the data collection unit.

In the processing in FIG. 11, first, in step S50, the data collection unit 52 calculates an area $S_{DW}$ of a window region $t_0$ to $t_1$. Here, "window region $t_0$ to $t_1$" means a region that is bounded by outer peripheral edges of all the windows displayed on the screen B during time from time $t_0$ to time $t_1$. Specifically, it is assumed that the state of the screen B at time $t_0$ is a state as illustrated in FIG. 12A, and the state of the screen B at time $t_1$ is a state as illustrated in FIG. 12B. In this case, the window region $t_0$ to $t_1$ is a region that is bounded by outer peripheral edges of the window ID: 1 displayed, and outer peripheral edges of the window ID: 2 displayed, which means a region illustrated by a bold line in FIG. 12C.

Next, in step S52, the data collection unit 52 calculates an area $S_{1W}$ of the window of the window ID: 1 at time $t_1$. Here, a window area of the window ID: 1 illustrated in FIG. 12B is calculated.

Figure 12E:
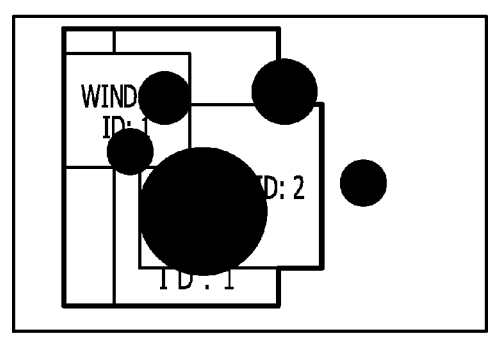

Next, in step S54, the data collection unit 52 calculates the total area (in addition to the overlapped area) $S_{ES}$ of the visual attention area estimation map included in the window region $t_0$ to $t_1$. Here, if it is assumed that five circles are recorded in the visual attention area estimation map at time $t_1$ as in FIG. 12D, as the area $S_{ES}$, an area of an overlapping portion with the window region $t_0$ to $t_1$ as illustrated in FIG. 12E is calculated among the five circles.

Next, in step S56, the data collection unit 52 calculates the total viewed area S of the content of the content ID=1 displayed in the window of the window ID: 1 on the screen B at the current time $t_1$. In this case, it is possible to calculate the total viewed area S allocated to the content of the content ID=1, which is displayed in the window of the window ID:

1 as the product of the area $S_{ES}$ and the ratio of the window area at time $t_1$ to the region bounded by outer peripheral edges of all the windows displayed during the time from time $t_0$ to time $t_1$, $S_{1W}/S_{DW}$ (allocation ratio). That is to say, it is possible for the data collection unit 52 to calculate the area S by Expression (1).

$$S = S_{ES} \times S_{1W}/S_{DW} \quad (1)$$

In this regard, FIG. 6 illustrates an example in which "8000" is calculated as a total area of viewed content.

Processing of Data Processing Unit 54

Next, a description will be given of processing of the data processing unit 54 with reference to a flowchart in FIG. 13. In this regard, the data processing unit 54 may perform the processing in FIG. 13 in same time phase with the calculation (FIG. 9) of the user's audio/visual action state variable, or may start the processing in same time phase with the content viewing end. Alternatively, the data processing unit 54 may perform the processing in FIG. 13 as periodical batch processing.

Figure 13:
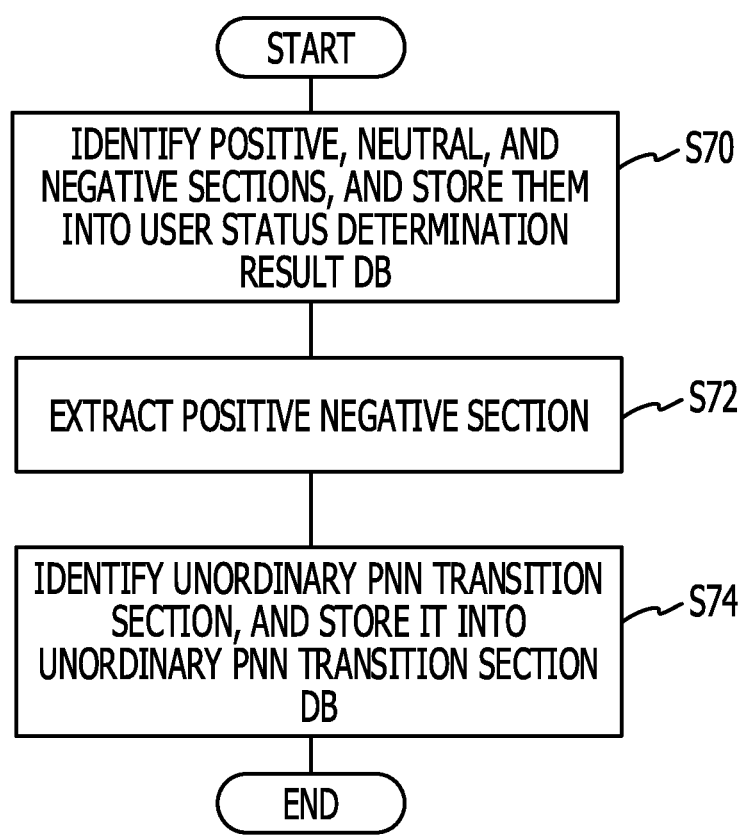
FIG. 13 is a flowchart illustrating processing of a data processing unit according to the first embodiment.

In the processing in FIG. 13, first, in step S70, the data processing unit 54 identifies a positive (P), a neutral (-), and a negative (N) content timeframes, and stores the timeframes into the user status determination result DB 44. For example, it is assumed that when the user status is positive at content viewing time, the posture change time becomes short, and when the user status is negative, the posture change time becomes long. In this case, it is possible to use the posture change time as a user's audio/visual action state variable value. If it is assumed that the user's audio/visual action state variable value S=posture change time $T_{trans}$, it is possible to represent a user status U in the form of U={Positive (S<2000), Negative (S>4000)}. Alternatively, it is possible to assume that if the user status is positive at content viewing time, the fixation time of the eye gaze is long, whereas if the user status is negative, the fixation time of the eye gaze is short. In this case, it is possible to use the fixation time of the eye gaze as the user's audio/visual action state variable value. If it is assumed that the user's audio/visual action state variable value S=fixation time of eye gaze $T_s$, it is possible to represent as in the form that the user status U={Positive (S>4000), Negative (S<1000)}. In this regard, in the first embodiment, a description will be given of the case of using the posture change time as the user's audio/visual action state variable value.

Next, in step S72, the data processing unit 54 extracts a timeframe (called a PNN section) in which a change occurs: positive→negative. Here, in the PNN section (during the content timeframes 5 to m in FIG. 7), although it is not possible to determine the user status to be positive nor negative, it is estimated that the value of the user's audio/visual action state variable value S monotonously increases with time passage.

Next, in step S74, the data processing unit 54 identifies an unordinary PNN transition section, and records it into the unordinary PNN transition section DB 45. In this regard, the unordinary PNN transition section means, in this case, a timeframe in which although a monotonous increase is estimated, a timeframe that indicates different transition. Also, in this timeframe, there is a possibility that an unordinary state of the user has occurred contrary to ordinary transition from positive to negative. Accordingly, in the present embodiment, this unordinary PNN transition section is regarded as a timeframe that has a high possibility of a timeframe (neutral plus section) in which the user becomes the positive state compared with the neighboring timeframe.

Figure 14:
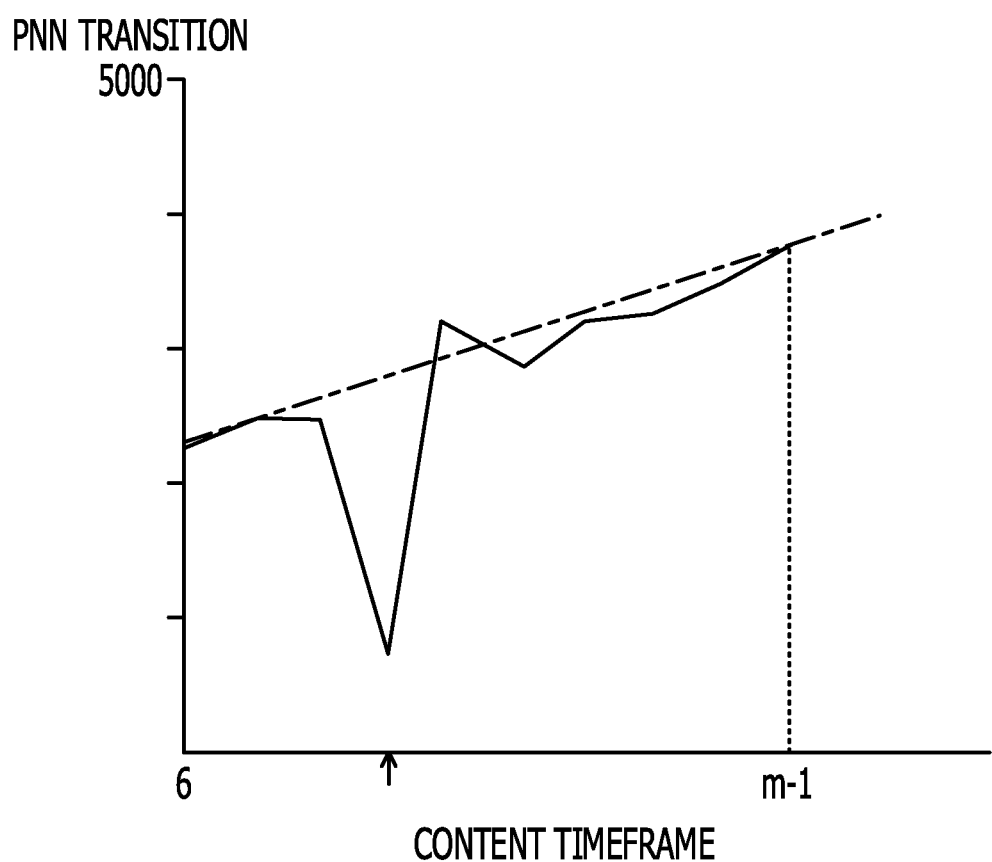
FIG. 14 is a graph illustrating a PNN transition value in an audio/visual digital content timeframe in which a user state is determined to be neutral.

Specifically, in step S74, the data processing unit 54 records a content timeframe i in which although $S_i > S_{i-1}$ ($S_i$: PNN transition value of the content timeframe i) is ordinarily supposed to hold in the PNN section, $S_i < S_{i-1}$ holds as an unordinary PNN transition section. In this regard, the PNN transition value means an index value indicating a positive state or a negative state of the user. In FIG. 14, the PNN transition values $S_6$ to $S_{m-1}$ between the content timeframes (PNN sections) 6 and (m−1) in which the user status is determined to be neutral, illustrated in FIG. 8, is represented by a line graph (solid line). Also, in FIG. 14, a line that linearly approximates a monotonous increase change of the PNN section is represented by a dashed-dotted line.

Here, in step S74, a degree of being out of ordinary in a certain timeframe is represented by a numeric value. As a numeric value in this case, it is possible to employ a degree of being out of ordinary timeframe represented by the difference between the linearly approximated value and the calculated value. In this case, if it is assumed that the absolute value differences between each PNN transition value and a linearly approximated value in the adjacent timeframes of the content timeframe i−1, the content timeframe i, and the content timeframe i+1 are $e_{i-1}$, $e_i$, and $e_{i+1}$, respectively, it is possible to represent the degree of being out of ordinary in the content timeframe i by the difference with the absolute value difference ordinarily assumed. Here, if it is assumed that the assumed absolute value difference is $(e_{i-1}+e_{i+1})/2$, the degree of being out of ordinary timeframe (degree of unordinary timeframe) $q_i$ of the content timeframe i is represented by $e_i-((e_{i-1}+e_{i+1})/2)$. Accordingly, it is possible for the data processing unit 54 to obtain the degree of being out of ordinary timeframe $q_i$ in each neutral plus section candidate (each timeframe in the PNN section) as a neutral plus estimation value $v_i$, and to determine that the timeframe is neutral plus section if a value $v_i$ is a certain value or more. In this regard, in the present embodiment, a timeframe indicated by an arrow in FIG. 14 (the content timeframe=9 in FIG. 8) is recorded as an unordinary PNN transition section (neutral plus section).

Figure 15A:
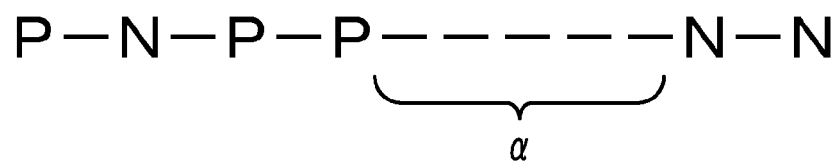
FIGS. 15A and 15B are explanatory diagrams of advantages of the first embodiment.
Figure 15B:
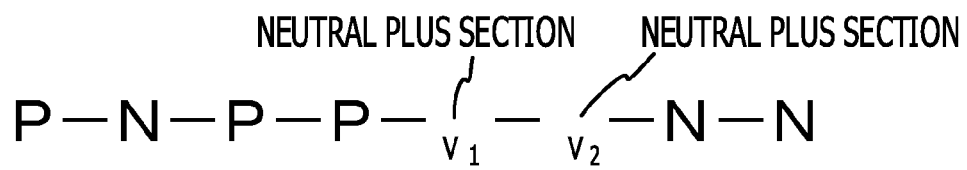

In this manner, in the present embodiment, as illustrated in FIG. 15A, even if there is an intermediate timeframe a between positive and negative (a timeframe that is neither positive nor negative), as illustrated in FIG. 15B, it is possible to represent a timeframe having a high possibility of the user becoming positive state by a neutral plus estimation value $v_i$. Also, in the present embodiment, it is possible to estimate a neutral plus section (unordinary PNN transition section) based on the neutral plus estimation value $v_i$, and thus it is possible to estimate the user state with high precision.

In this regard, the server 10 uses the data stored or recorded in the user status determination result DB 44 and the unordinary PNN transition section DB 45 as described above. Accordingly, for example, it is possible to create an abridged version of a content using content images of a positive section and a neutral plus section, and so on. Also, it is possible to provide (feedback) a content creator (a lecturer, and so on) with information on timeframes in which the user had an interest or attention, and timeframes in which the user had no interest or attention, and so on. In this manner, in the present embodiment, it is possible to evaluate, and reorganize a content, and to perform statistics processing on a content, and so on.

In this regard, in the present embodiment, the data processing unit 54 achieves functions of an identification unit that identifies a PNN section from a detection result of a positive state and a negative state of a user who is viewing a content, an extraction unit that extracts a timeframe in which an index value (PNN transition value) representing a positive or negative state of the user indicates an unordinary value in the identified PNN section, and an estimation unit that estimates the extracted timeframe as a neutral plus section.

As described above in detail, by the first embodiment, the data processing unit 54 identifies a timeframe (PNN section) in which the user status is allowed to be identified as neither positive (P) nor negative (N) in the detection result of the state of the user viewing a content, extracts a time period in which the PNN transition value of the user indicates an unordinary value (a time period indicating different tendency from a monotonous increase or a monotonous decrease) in the identified PNN section, and estimates that the extracted time period is a time period (neutral plus section) having a high possibility of the user having been in a positive or a negative state. Thereby, even in the case where it is difficult to determine whether the user has an interest or attention (a case of viewing e-learning or a moving image of a lecture, and so on), it is possible to estimate a timeframe having a high possibility that the user had an interest or attention.

Also, in the present embodiment, it is possible to estimate a timeframe having a high possibility of the user having an interest or attention using a simple apparatus, such as a Web camera, and so on. Accordingly, a special sensing device does not have to be introduced, and thus it is possible to reduce cost.

In this regard, in the above-described embodiment, a description has been given of the case where a positive or negative section is identified using the attentive audience sensing data in step S70 in FIG. 13. However, the present disclosure is not limited to this, and the data processing unit 54 may identify a positive or negative section using data obtained by directly hearing from the user.

Also, in the above-described embodiment, a description has been given of the case of using one kind of data as a user's audio/visual action state variable. However, the present disclosure is not limited to this, and user's audio/visual action state variables of a plurality of persons may be used in combination (for example, representing by a polynomial, and so on).

In this regard, in the above-described embodiment, a description has been given of the case where an unordinary section is estimated in a timeframe of changing from positive to negative (PNN section). However, the present disclosure is not limited to this, and the unordinary section may be estimated in a timeframe of changing from negative to positive.

Second Embodiment

Figure 16A:
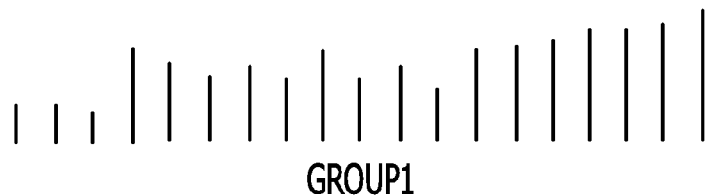
FIGS. 16A, 16B and 16C are explanatory diagrams of an example of grouping according to a second embodiment.
Figure 16B:
Figure 16C:
Figure 17:
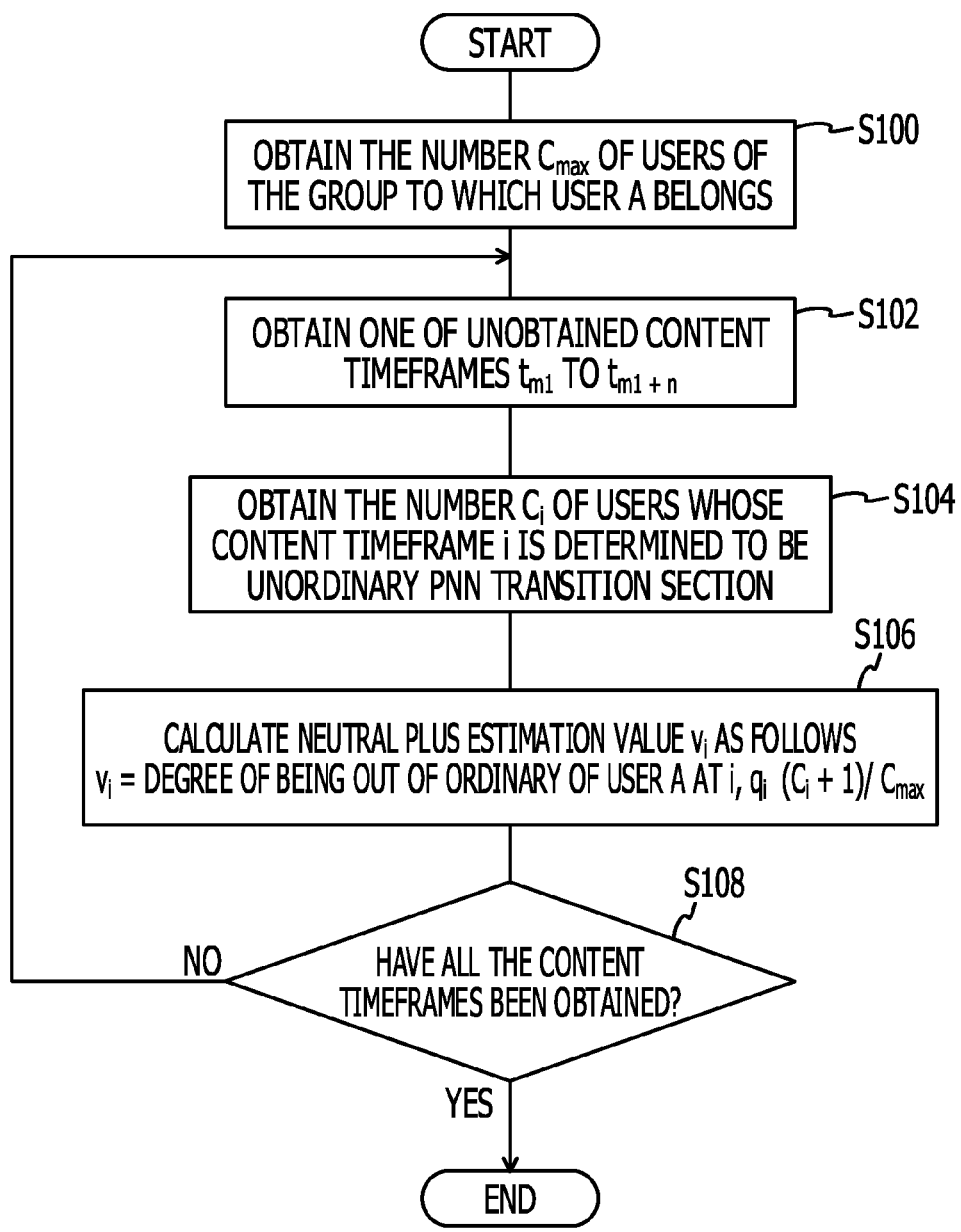
FIG. 17 is a flowchart illustrating processing of a data processing unit according to the second embodiment.

In the following, a description will be given of a second embodiment with reference to FIG. 16 and FIG. 17. In the second embodiment, the data processing unit 54 in FIG. 3 divides a plurality of users into a plurality of groups, and performs determination processing of the unordinary PNN transition section of a content based on the state (a positive state or a negative state) of the users who belong to that group.

In the case where a plurality of users view a content (for example, e-learning and a lecture video), it is possible for the data collection unit 52 to collect a large amount of data of the user states at content viewing time. Accordingly, it is possible for the data processing unit 54 to classify users who have completed viewing into several groups using the large amount of collected user's audio/visual action state variables. FIGS. 16A, 16B and 16C illustrates an example of classifying user groups in the case of using posture changes as the user's audio/visual action state variable. One vertical bar in FIG. 16 illustrates a posture change time in a certain timeframe. In this classification example, attention is focused on transition tendency from a timeframe (positive) having a short posture change time to a timeframe (negative) having a long posture change time: positive neutral negative. FIG. 16A illustrates an example of a group having a long neutral time, FIG. 16B illustrates an example of a group having a long negative time, and FIG. 16C illustrates an example of a group having a long positive time.

In this regard, the data processing unit 54 may perform grouping using data of all the timeframes during viewing of one content at the time of grouping, or may perform grouping on the users having transition of user states by focusing attention on a specific timeframe of a specific content in the same manner. Alternatively, the data processing unit 54 may perform grouping by a common posture change pattern (the number of posture change times significantly decreases in the latter half of a content, and so on) without identifying a content. In either case, users having similar tendency of user's audio/visual action state variable transition are grouped together.

In the following, a description will be given of the processing of the data processing unit 54 according to the second embodiment with reference to a flowchart in FIG. 17.

In this regard, in the second embodiment, it is assumed that n neutral plus estimation values are calculated from user A during a PNN section k (content ID=1, content timeframes $t_{m1}$ to $t_{m1+n}$). Also, it is assumed that user A is classified into a user group 1 (neutral time is long).

First, in step S100, the data processing unit 54 obtains the number of users $C_{max}$ of the group to which the user A belongs.

Next, in step S102, the data processing unit 54 obtains an unobtained content timeframe i among content timeframes $t_{m1}$ to $t_{m1+n}$. Next, in step S104, the data processing unit 54 obtains the number of users $C_i$ whose content timeframe i is an unordinary PNN transition section.

Next, in step S106, the data processing unit 54 calculates the neutral plus estimation value $v_i$ by Expression (2). In this regard, $q_i$ means a degree of being out of ordinary timeframe of the user A in the content timeframe i.

$$v_i = q_i \times (C_i + 1)/C_{max} \quad (2)$$

As Expression (2), in the present embodiment, in the calculation of the neutral plus estimation value, a ratio of the number of users determined to be in the unordinary PNN transition section in each content timeframe in a group is used as a weight. Thereby, as a timeframe that is determined to have an unordinary PNN transition among the users in a same group in common, a higher value is calculated as a neutral plus estimation value. In this manner, in the present embodiment, in the over-all length of the PNN section, a timeframe in which there was movement determined to have positive tendency in common among the user A and the group to which the user A belongs is estimated to be a neutral plus section so that it is possible to estimate a user state in consideration of the group tendency.

After that, in step S108, a determination is made of whether all the content timeframes have been obtained. If it is determined that all the content timeframes have not been obtained, the processing returns to step S102. And the processing and the determination after step S102 are repeated. At the time when it is determined that all the content timeframes have been obtained in step S108, all the processing in FIG. 17 is terminated.

In this regard, in the second embodiment, the data processing unit 54 achieves the functions of the grouping execution unit that groups a plurality of users who view a content, the identification unit that identifies a PNN section in which a specific user (user A) state is determined to be neither positive nor negative, and the estimation unit that determines, in the over-all length of the PNN section, a timeframe in which there was movement determined to have positive tendency in common among a specific user and the group to which the specific user belongs, and estimates the timeframe to be a neutral plus section.

In the above, as described above, in the second embodiment, the data processing unit 54 identifies a PNN section of the user A, and estimates, in the over-all length of the PNN section, a timeframe in which there was movement determined to have positive tendency in common among the user A and the group to which the user A belongs (a timeframe having a high neutral plus estimation value $v_i$) to be a neutral plus section. Thereby, it is possible to estimate a user state in consideration of group tendency having user state transition in the same manner, and thus it is possible to make an estimation of minute user state change with high precision.

Third Embodiment

Next, a description will be given of a third embodiment with reference to FIG. 18 and FIG. 19. In the third embodiment, the data processing unit 54 performs correction of a neutral plus estimation value using not only the information of the group to which the user belongs, but also the information of the other groups. In this regard, in the present embodiment, it is assumed that the user A of the client 20 displays the content ID=1 on the screen B in the same manner as the second embodiment. Also, in the present embodiment, a description will be given of the case where n neutral plus estimation values of the PNN section k (the content timeframes $t_{m1}$ to $t_{m1+n}$) are calculated.

In the present embodiment, the PNN transition values of the other groups 2 and 3 are referenced using not only the group 1 to which the user A is classified, but also data of the content timeframes $t_{m1}$ to $t_{m1+n}$. Here, FIG. 18 illustrates determination results of the unordinary PNN transition section for each individual groups, which are totaled in the content timeframes $t_{m1}$ to $t_{m1+n}$. In FIG. 18, it is assumed that the degree of being out of ordinary of the content timeframe i of each group is determined using the average value of the data of the users who belong to each group. In this regard, as a method of obtaining degree of being out of ordinary in the content timeframe i, a method of using a local maximal value or a median, and the like of the data of the users who belong to each group may be employed. Also, a numeric value, such as [0.1], and so on in FIG. 18 indicates a ratio of the users determined to be an ordinary section when a determination of the unordinary PNN transition section is performed using data of each single user in each group. The determination of the unordinary section is performed using the user's audio/visual action state variables, and thus it is assumed that there are cases where it is difficult for a group to be determined to be the unordinary section. For example, as an example in posture change, a case of a group having substantially no posture change in the PNN section, and so on.

In the third embodiment, the data processing unit 54 performs processing for correcting biased determination among these groups.

Figure 19:
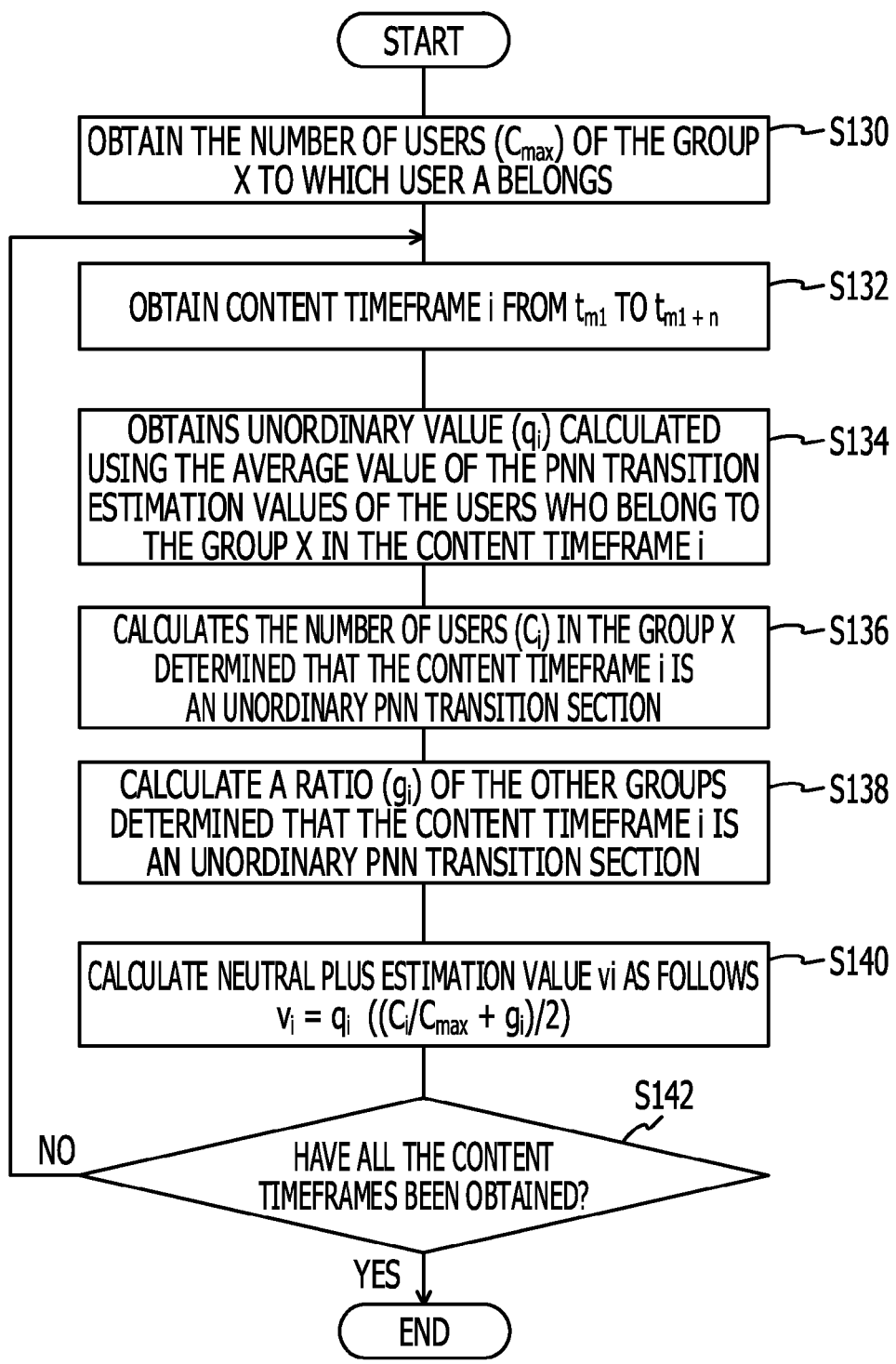
FIG. 19 is a flowchart illustrating processing of a data processing unit according to a third embodiment.

FIG. 19 is a flowchart illustrating processing of the data processing unit 54 according to the third embodiment. In the following, a description will be given of the processing of the data processing unit 54 with reference to FIG. 19.

In the processing in FIG. 19, first, in step S130, the data processing unit 54 obtains the number of users ($C_{max}$) of the group X to which the user A belongs. Next, in step S132, data processing unit 54 obtains an unobtained content timeframe i during the content timeframes $t_{m1}$ to $t_{m1+n}$.

Next, in step S134, the data processing unit 54 obtains the degree of being out of ordinary timeframe ($q_i$) calculated using the average value of the PNN transition values of the users who belong to the group X in the content timeframe i. In this regard, it is possible to determine whether the content timeframe i is an unordinary PNN transition section or not by the degree of being out of ordinary timeframe ($q_i$).

Next, in step S136, the data processing unit 54 calculates the number of users ($C_i$) in the group X determined that the content timeframe i is the unordinary PNN transition section.

Next, in step S138, the data processing unit 54 calculates a ratio ($g_i$) of the other groups having the content timeframe i determined to be the unordinary PNN transition section. In this case, for example, if the content timeframe i is the unordinary PNN transition section in all the other groups, $g_i$ becomes 1.

Next, in step S140, the data processing unit 54 calculates the neutral plus estimation value $v_i$ by Expression (3).

$$v_i = q_i \times ((C_i/C_{max} + g_i)/2) \quad (3)$$

In this case, if the value $v_i$ is a certain value or more, it is possible to determine that the timeframe is a neutral plus section.

In this manner, in the present embodiment, the neutral plus estimation value $v_i$ is calculated using, as weights, the ratio ($C_i/C_{max}$) of the user determined to be an unordinary PNN transition section in the group to which the user to be determined belongs, and the ratio ($g_i$) of the group determined to be an unordinary PNN transition section among the other groups. Thereby, a higher value is calculated as a neutral plus estimation value in a timeframe in which the PNN transition is determined to be unordinary among the users of the same group in common, and the PNN transition is determined to be unordinary among the other groups in common.

Next, in step S142, the data processing unit 54 determines whether all the content timeframes have been obtained. If it is determined that all the content timeframes have not been obtained, the processing proceeds to S132, obtains unobtained content timeframes i, and the above-described processing is repeated. On the other hand, if it is determined that all the content timeframes have been obtained in step S142, the entire processing in FIG. 19 is terminated.

In the above, as described, by the third embodiment, a neutral plus estimation value $v_i$ is calculated in consideration of not only the group to which the user belongs, but also the other groups so that it is possible to estimate a neutral plus section with higher precision.

Fourth Embodiment

Next, a description will be given of a fourth embodiment with reference to FIG. 20 and FIG. 21. In the fourth embodiment, the data processing unit 54 determines the unordinary PNN transition section using the PNN transition value by the use of selected data (data of a user having a certain attribute (for example, a person in his fifties who is working at Shiodome head office, and so)) so as to identify a timeframe having a high neutral plus estimation value that is specific to the selected data.

The server 10 collects data of a plurality of users, and performs processing by selecting data of only users having a user attribute C in order to identify a timeframe having high possibility of being positive (the timeframe having a high neutral plus estimation value) for the users with a user attribute (for example, an attribute C) in the time period of the content timeframes $t_{m1}$ to $t_{m1+n}$.

Figure 20:
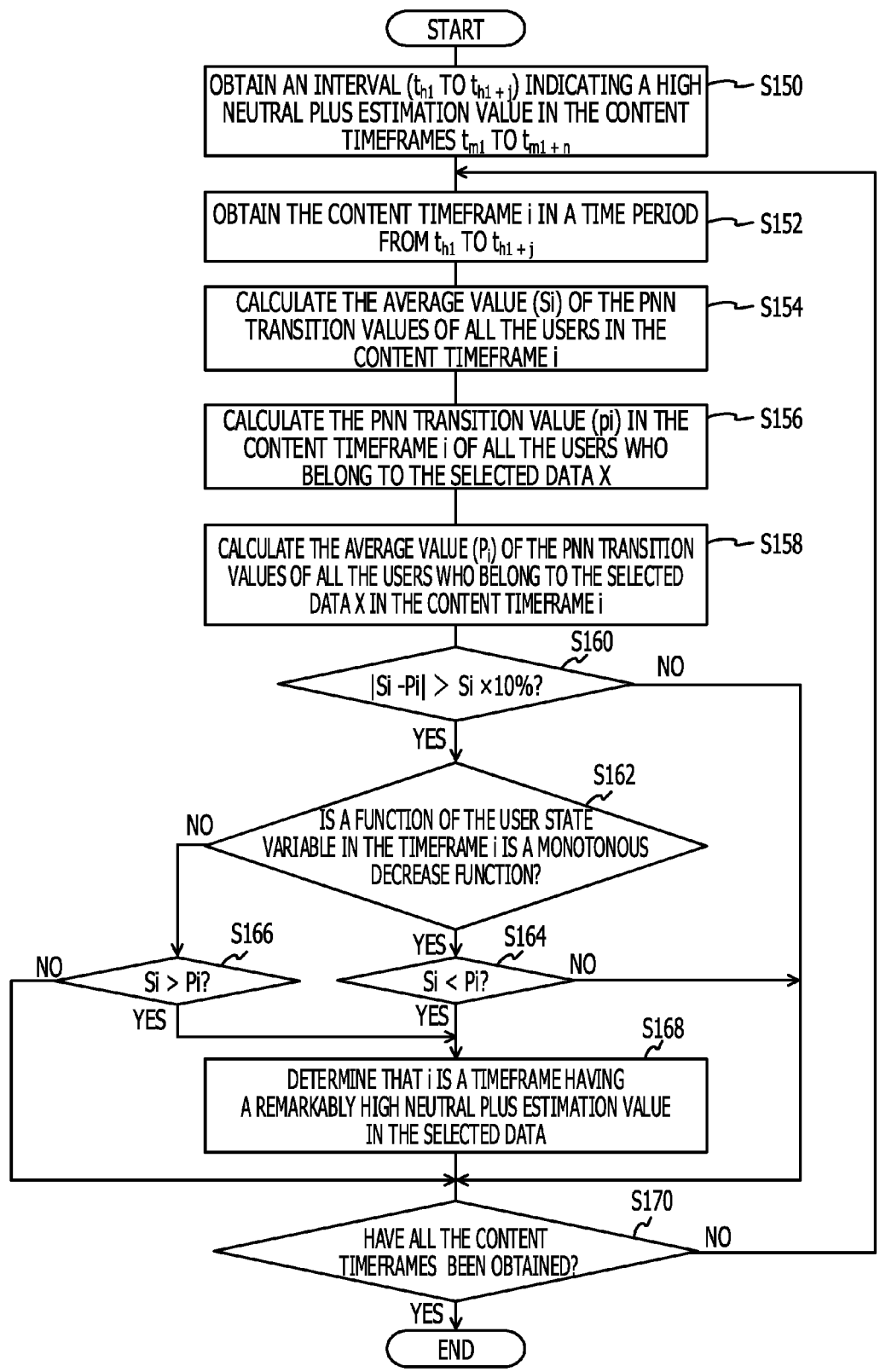
FIG. 20 is a flowchart illustrating processing of a data processing unit according to a fourth embodiment.

FIG. 20 illustrates processing of the data processing unit 54 according to the fourth embodiment. In the following, a description will be given of the processing of the data processing unit 54 with reference to FIG. 20. In this regard, at a stage of starting the processing in FIG. 20, it is assumed that the data processing unit 54 is identifying the timeframe ($t_{h1}$ to $t_{h1+j}$) indicating a high neutral plus estimation value using data of a plurality of users in the same manner as in the first embodiment, and so on. In this regard, the i-th and the (i+1)-th timeframes ($t_i$ and $t_{i+1}$) are in chronological order. However, $t_{i+1}$ may be not immediately after t. Also, at $t_i$ and at $t_{i+1}$, data may be of cases where separate contents were viewed.

In the processing in FIG. 20, first, in step S150, the data processing unit 54 obtains a timeframe ($t_{h1}$ to $t_{h1+j}$) indicating a high neutral plus estimation value during the content timeframes $t_{m1}$ to $t_{m1+n}$.

Next, in step S152, the data processing unit 54 obtains the content timeframe i during a time period from $t_{h1}$ to $t_{h1+j}$. Next, in step S154, the data processing unit 54 calculates the average value ($S_i$) of the PNN transition values of all the users in the content timeframe i. In FIG. 21, $S_i$, which was calculated in step S152, is stored in the field of "original data".

Next, in step S156, the data processing unit 54 calculates the PNN transition value ($p_i$) in the content timeframe i of all the users (all the users having an attribute C) who belong to the selected data (assumed to be data X).

Next, in step S158, the data processing unit 54 calculates the average value ($P_i$) of the PNN transition values of all the users who belong to the selected data X in the content timeframe i. In FIG. 21, $P_i$, which was calculated in step S158, is stored in the field of "selected data".

Next, in step S160, the data processing unit 54 determines whether the following expression holds or not: $|S_i - P_i| > S_i \times 10\%$. In this regard, in step S160, a determination is made of whether there is a sufficient difference between the original data and the selected data. Here, if it is determined that the expression is not held, the processing proceeds to step S170, whereas if it is determined that the expression is held (if there is a sufficient difference), the processing proceeds to step S162. In this regard, in FIG. 21, it is assumed to have determined that there is a sufficient difference in the timeframe $t_{h1+1}$.

When the processing proceeds to step S162, the data processing unit 54 determines whether a function of the user's audio/visual action state variable in the timeframe i is a monotonous decrease function or not. Here, if it is determined that the function of the user's audio/visual action state variable in the timeframe i is the monotonous decrease function, the processing proceeds to step S164, and the data processing unit 54 determines whether $S_i < P_i$. For example, in the case of monotonous decrease in the timeframe $t_{h1+1}$ in FIG. 21, and thus the processing proceeds to step S168. When the processing proceeds to step S168, the data processing unit 54 determines that the timeframe i is a timeframe having a remarkably high neutral plus estimation value in the selected data (refer to the field of "attribute that is remarkably positive than neutral" in the timeframe $t_{h1+1}$ in FIG. 21). After that, the processing proceeds to step S170. On the other hand, if it is determined that $S_i < P_i$ is held in step S164, the processing proceeds to step S170 without going through step S168.

On the other hand, in step S162, if it is determined that the user's audio/visual action state variable in the timeframe i is not a monotonous decrease function, the data processing unit 54 proceeds to step S166. In step S166, the data processing unit 54 determines whether $S_i > P_i$. If it is determined that $S_i > P_i$ is held, the processing proceeds to step S168, and in the same manner as above, the data processing unit 54 determines that the timeframe i is a timeframe having a remarkably high neutral plus estimation value in the selected data, and the processing proceeds to step S170. On the other hand, if it is determined that $S_i > P_i$ is not held in step S166, the processing proceeds to step S170 without going through step S168.

When the processing proceeds to step S170, the data processing unit 54 determines whether all the content timeframes have been obtained. If it is determined that all the content timeframes have not been obtained, the processing proceeds to step S152, obtains an unobtained content timeframe and the above-described processing is repeated. On the other hand, if it is determined that all the content timeframes have been obtained in step S170, all the processing in FIG. 20 is terminated.

In this regard, in the fourth embodiment, the significant differences of the PNN transition values are compared between the selected data and the original data by limiting to timeframes $t_{h1}$ to $t_{h1+j}$ having the high neutral plus estimation value. However, the significant differences may be compared among the timeframes of all the PNN sections.

In this regard, in the fourth embodiment, the data processing unit 54 achieves the functions of a selection unit that selects a part of a plurality of users, and a comparison unit that estimates a timeframe having a high possibility of the selected user having been in a positive or a negative state using the detection result of the state of the selected user, and compares with the estimation result of the estimation unit.

As described above, by the fourth embodiment, it is possible to identify a timeframe having a possibility of being remarkably positive on a certain attribute. Thereby, it is possible to identify a part of a content in which a user having a certain attribute has an interest or attention in particular with high precision.

Fifth Embodiment

In the following, a description will be given of a fifth embodiment with reference to FIG. 22 and FIG. 23. In the fifth embodiment, at the time of determining the unordinary PNN transition section, the data processing unit 54 determines the unordinary PNN transition section for each of the timeframes having multiple constant period.

In the fifth embodiment, it is assumed that in the same manner as the second embodiment, and so on, a user A of the client 20 is displaying a content of the content ID=1 on the screen B. Also, in the fifth embodiment, it is assumed that the data processing unit 54 calculates a neutral plus estimation value of the user A during a PNN section k (content ID=1, and the content timeframes $t_{m1}$ to $t_{m1+n}$). Also, it is assumed that a posture change is used as a user's audio/visual action state variable in the PNN estimation value calculation.

Here, posture change (transition of posture) itself does not change simply from a close side of the screen to a far side in the PNN section. In particular, if the user loses an interest in a content, it is thought that the user often reveals small movements restlessly. That is to say, a little posture movement is sometimes observed at the same time in addition to transition from a close side to a far side from a screen in the PNN section.

Accordingly, if a determination is made of the unordinary PNN transition section after a PNN transition value is calculated, there are cases where a determination result is different depending on which constant period is used for comparison. Accordingly, in the fifth embodiment, in the determination of the unordinary PNN transition section, PNN transition values are compared using multiple constant period as an observation timeframe in order to determine the unordinary PNN transition section.

Figure 22:
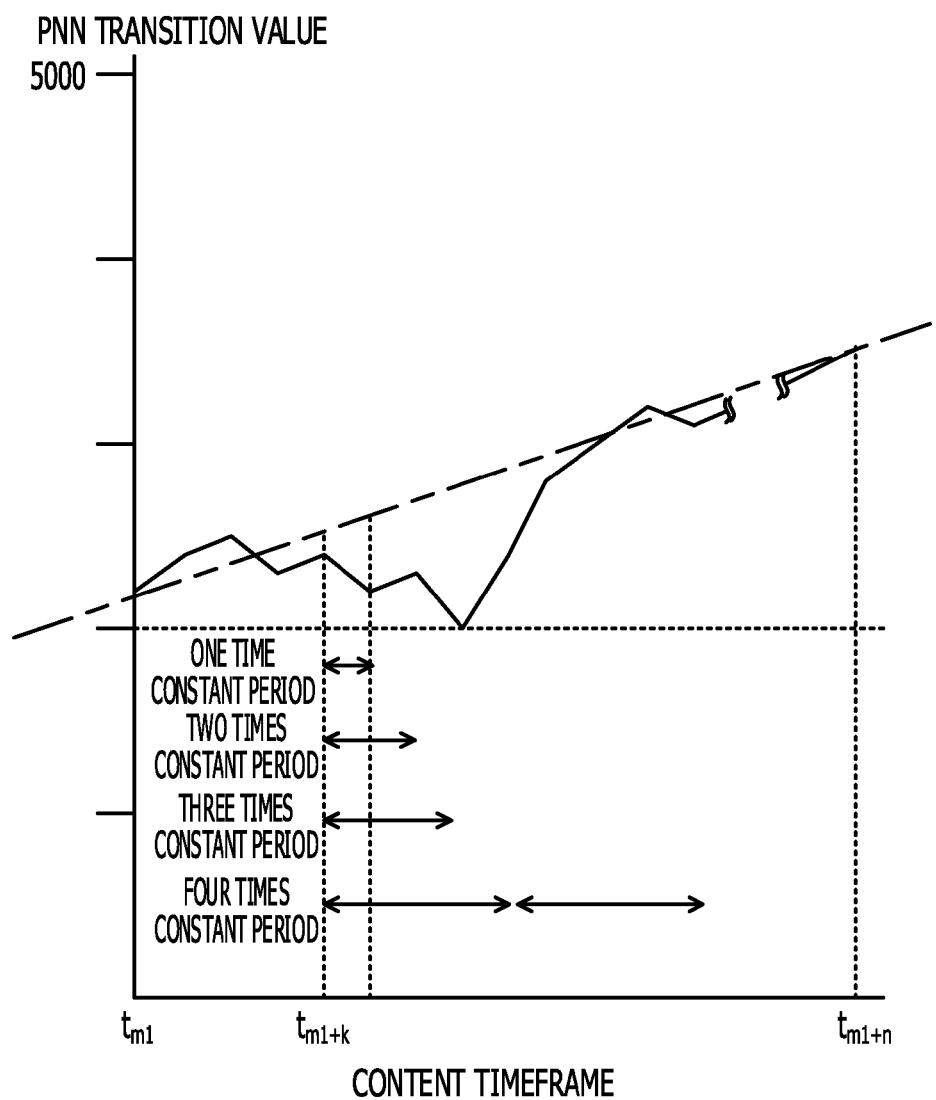
FIG. 22 is a diagram illustrating an example of a PNN transition value according to a fifth embodiment.

FIG. 22 illustrates an example of a PNN transition value used in the fifth embodiment. Also, FIG. 23 illustrates an example of comparison of PNN transition values and determination results of the unordinary PNN transition section in multiple constant period. In this regard, in FIG. 23, a constant period based on the determination of the unordinary PNN transition section is described together.

In these figures, a comparison is made of how degrees of being out of ordinary timeframes are different in one time constant period and four times constant period by focusing attention on the timeframe $t_{m1+k}$. Here, in order to calculate a neutral plus estimation value, a degree of being out of ordinary timeframe is directly used without a weight in the same manner as the first embodiment.

In one time constant period, there is not so much difference with an approximation function value in the case of a neighboring timeframe, and thus in a change of the PNN transition value as illustrated in FIG. 22, it is difficult to understand that a change has occurred in this timeframe. In contrast, in four times constant period, the PNN transition value has dropped to a value near to the value at time $t_{m1}$, and thus it is understood that this is a timeframe having a relatively large degree of being out of ordinary.

In this manner, in the fifth embodiment, the degree of being out of ordinary is determined by a constant period in which changes to be detected occur consecutively so that it becomes possible to detect desired degree of being out of ordinary. In this regard, there are various time constant periods of a change to be detected, and thus degree of being out of ordinary may be determined in multiple constant period, or a comprehensive method, such as a method of comparing degree of being out of ordinary in all the integer multiples of a contrast period, may be employed.

Also, in the fifth embodiment, the PNN transition value of the m-times contrast period is represented by the average value. However, a local maximal value or a local minimal value may be used as a representative value of the timeframe. Also, a degree of being out of ordinary timeframe for each of a plurality of one time, two times, . . . and m-times constant period, which was obtained here, is a value calculated in order to determine the degree of being out of ordinary of one-time constant period to be a reference. In the case where it is not preferable to use the average value of the data of the other timeframes or a local extreme value of the timeframe in order to determine the degree of being out of ordinary of the timeframe, a degree of being out of ordinary timeframe at m-times constant period may be calculated using a coefficient that shows the inclination of the line for linear approximation of a change graph of the PNN transition value in a timeframe adjacent to the m-times constant period, and so on in place of the PNN transition value.

As described above, by the fifth embodiment, the degree of being out of ordinary is detected in multiple constant period, and thus even when a large movement and a small movement are observed at the same time just like a posture change, it is possible to determine the unordinary PNN transition section with high precision. Also, in the fifth embodiment, a constant period to be grounds is also recorded as a determination result of the unordinary section (FIG. 23), and thus the grounds for determining the unordinary PNN transition section (what posture change causes to determine the unordinary PNN transition section) are apparent. Thereby, when a determination result of the unordinary PNN transition section is used, it becomes possible to make use of the determination result based on the grounds.

In this regard, in each of the above-described embodiments, a description has been given of the case where the server 10 and the client 20 are separate apparatuses. However, the present disclosure is not limited to this, the server software and the client software may be implemented in one apparatus, and the one apparatus may achieve the functions of the server 10 and the client 20.

Also, the functions of one software system may be distributed in a plurality of apparatuses. For example, a part of the functions of the server 10 and the client 20, or a part of data may be held separately in the other apparatus, and so on.

In this regard, it is possible to achieve the above-described processing functions by a computer. In that case, the program describing the processing contents of the functions of the processing apparatus is provided. By executing the program on a computer, the above-described processing functions are achieved on the computer. It is possible to record the program describing the processing contents in a computer readable recording medium (however, a carrier wave is excluded).

In the case of distributing the program, the program is marketed in the form of a portable recording medium, for example, a digital versatile disc (DVD) on which the programs are recorded, a compact disc read only memory (CD-ROM), and so on. Also, it is possible to store the program in a storage device of a server computer, and to transfer the program from the server computer to the other computers through a network.

A computer that executes the program stores, for example, the program recorded in a portable recording medium or the program transferred from a server computer into its own storage device. And the computer reads the program from the own storage device, and executes processing in accordance with the program. In this regard, it is possible for the computer to directly read the program from the portable recording medium, and execute processing in accordance with the program. Also, it is possible for the computer to execute processing in accordance with the received program one after another each time the program is transferred from the server computer.

The above-described embodiments are examples of preferable modes for carrying out the present disclosure. However, the present disclosure is not limited to this. Various variations are possible without departing from the spirit at the scope of the present disclosure.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A method of processing information, the method comprising:
by at least one hardware processor that executes instructions stored in a memory to cause,
obtaining stored information indicating correspondences of content time frames indicating time spans for a content viewed by a user and an attention status of the user to the viewed content in a content time frame among the content time frames, the attention status of the user determined from among attention statuses of positive, negative or neutral based on detection results of behavioral states of the user viewing the content in the time spans corresponding to the content time frames;
extracting, from among the content time frames in the stored information indicating the correspondences, a plurality of adjacent content time frames corresponding to a plurality of neutral attention states between content time frames corresponding to other than neutral attention states of the user;
determining, from among the extracted adjacent content time frames corresponding to the neutral attention states, at least one unordinary attention state transition value indicating at least one unordinary attention state of the user according to a degree of change in an attention state transition value with respect to other attention state transition values of other content time frames in the extracted adjacent content time frames; and
in response to the determining of the at least one unordinary attention state of the user, estimating, according to the content time frames in the stored information indicating the correspondences, a content time span of at least one content time frame during the extracted adjacent content time frames which the user has the at least one unordinary attention state,
wherein viewed content of the estimated content time frame is used for generation of related content to the viewed content.

2. The method of processing information according to claim 1, wherein:
the information indicating the correspondences includes information of a plurality of users;
the extracting includes extracting a group of the users including the user viewing the content; and
the determining of the unordinary attention state of the user in the extracted adjacent content time frames includes using as a computation weight a ratio of users in the group of users having the unordinary attention state in common with the user.

3. The method of processing information according to claim 2, wherein:
the executing of the instructions by the at least one hardware processor further cause grouping the users in the information indicating the correspondences into a plurality of user groups;
the determining of the unordinary attention state of the user in the extracted adjacent content time frames includes using as a computation weight a ratio of users in at least one other user group among the user groups having the unordinary attention state in common with the user.

4. The method of processing information according to claim 2, wherein:
the stored information indicating the correspondences includes attribute information of the users;
the executing of the instructions by the at least one hardware processor further cause grouping the users in the information indicating the correspondences into a plurality of user groups according to the attribute information of the users;
the determining of the unordinary attention state transition value is determined for a selected number of user groups among the user groups;
the estimating includes estimating content time frames during the extracted adjacent content time frames for the selected user groups; and
comparing results of the estimating to determine the estimated content time frame among the estimated content time frames.

5. An information processing apparatus comprising:
at least one memory to store information and instructions; and
at least one hardware processor coupled to the memory to execute the instruction to cause the information processing apparatus to:
obtain stored information indicating correspondences of content time frames indicating time spans for a content viewed by a user and an attention status of the user to the viewed content in a content time frame among the content time frames, the attention status of the user determined from among attention statuses of positive, negative or neutral based on detection results of behavioral states of the user viewing the content in the time spans corresponding to the content time frames,
extract, from among the content time frames in the stored information indicating the correspondences, a plurality of adjacent content time frames corresponding to a plurality of neutral attention states between content time frames corresponding to other than neutral attention states of the user;
determine, from among the extracted adjacent content time frames corresponding to the neutral attention states, at least one unordinary attention state transition value indicating at least one unordinary attention state of the user according to a degree of change in an attention state transition value with respect to other attention state transition values of other content time frames in the extracted adjacent content time frames, and
in response to the determination of the unordinary attention state of the user, estimate, according to the content time frames in the stored information indicating the correspondences, a content time span of at least one content time frame during the extracted adjacent content time frames which the certain user has the at least one unordinary attention state,
wherein viewed content of the estimated content time frame is used to for generation of related content to the viewed content.

6. The information processing apparatus according to claim 5, wherein:
the information indicating the correspondences includes information of a plurality of users;

the extracting includes extracting a group of the users including the user viewing the content; and the determining of the unordinary attention state of the user in the extracted adjacent content time frames includes using as a calculation weight a ratio of users in the group of users having the unordinary attention state in common with the user.

7. The information processing apparatus according to claim 5, wherein:

the stored information indicating the correspondences includes attribute information of the users;

the executing of the instructions by the at least one hardware processor further cause grouping the users in the information indicating the correspondences into a plurality of user groups according to the attribute information of the users;

the determining of the unordinary attention state transition value is determined for a selected number of user groups among the user groups;

the estimating includes estimating time periods during the extracted adjacent content time frames for the selected user groups; and comparing results of the estimating to determine the estimated content time frame among the estimated content time frames.

8. The method of processing information according to claim 1, wherein the extracting extracts a plurality of sets of adjacent content time frames corresponding to a plurality of neutral attention states between content time frames corresponding to other than neutral attention states of the user; and the determining of the unordinary attention state transition value is according to the plurality of sets of the extracted adjacent content time frames.

9. The information processing apparatus according to 5, wherein the extracting extracts a plurality of sets of adjacent content time frames corresponding to a plurality of neutral attention states between content time frames corresponding to other than neutral attention states of the user; and the determining of the unordinary attention state transition value is according to the plurality of sets of the extracted adjacent content time frames.

* * * * *